United States Patent
Ito et al.

(10) Patent No.: US 10,858,391 B2
(45) Date of Patent: Dec. 8, 2020

(54) METHOD FOR PURIFYING COMPOSITION COMPRISING ANTIBODIES WITH ANIONIC POLYMER

(71) Applicant: Chugai Seiyaku Kabushiki Kaisha, Tokyo (JP)

(72) Inventors: Seiya Ito, Tokyo (JP); Akihiro Yanagita, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 176 days.

(21) Appl. No.: 15/748,736

(22) PCT Filed: Jul. 29, 2016

(86) PCT No.: PCT/JP2016/072270
§ 371 (c)(1),
(2) Date: Jan. 30, 2018

(87) PCT Pub. No.: WO2017/022651
PCT Pub. Date: Feb. 9, 2017

(65) Prior Publication Data
US 2019/0010188 A1   Jan. 10, 2019

(30) Foreign Application Priority Data

Jul. 31, 2015 (JP) .................................. 2015-151981

(51) Int. Cl.
| | |
|---|---|
| C07K 1/30 | (2006.01) |
| C07K 16/06 | (2006.01) |
| C07K 1/18 | (2006.01) |
| C07K 16/28 | (2006.01) |
| C07K 16/36 | (2006.01) |
| C07K 16/00 | (2006.01) |

(52) U.S. Cl.
CPC .................. *C07K 1/18* (2013.01); *C07K 1/30* (2013.01); *C07K 16/00* (2013.01); *C07K 16/065* (2013.01); *C07K 16/2866* (2013.01); *C07K 16/36* (2013.01); *C07K 2317/24* (2013.01); *C07K 2317/31* (2013.01); *C07K 2317/94* (2013.01)

(58) Field of Classification Search
None
See application file for complete search history.

(56) References Cited

U.S. PATENT DOCUMENTS 8,163,886 B2 * 4/2012 Moya ....................... C07K 1/30
424/176.1

FOREIGN PATENT DOCUMENTS

| EP | 2644698 A | 10/2013 |
|---|---|---|
| JP | 19910516509 | 10/1991 |
| JP | H05504579 A | 7/1993 |
| JP | 2638680 B2 | 8/1997 |
| WO | WO-9207084 A1 | 4/1992 |
| WO | WO 9207084 A1 | 4/1992 |
| WO | WO-2008079302 A2 * | 7/2008 ............ C07K 16/00 |
| WO | WO-2008091740 A2 | 7/2008 |
| WO | WO-2009016449 A1 | 2/2009 |
| WO | WO-2010074702 A1 * | 7/2010 ............... C07K 1/32 |
| WO | WO-2015099165 A1 | 7/2015 |

OTHER PUBLICATIONS

Sieberz, J., et al., "Identification of parameter interactions influencing the precipitation of a monoclonal antibody with anionic polyelectrolytes," Separation and Purification Technology 127:165-173 (2014).
Sieberz, J., et al., "The influence of impurity proteins on the precipitation of a monoclonal antibody with an anionic polyelectrolyte," Separation and Purification Technology 146:252-260 (2015).
McDonald, P., et al., "Selective Antibody Precipitation Using Polyelectrolytes: A Novel Approach to the Purification of Monoclonal Antibodies," Biotechnol Bioeng 102(4):1141-1151 (2009).
Kang, Y., et al., "Development of a Novel and Efficient Cell Culture Flocculation Process Using a Stimulus Responsive Polymer to Streamline Antibody Purification Processes," Biotechnol Bioeng 110(11):2928-2937 (2013).
Brodsky, Y., et al., "Caprylic Acid Precipitation Method for Impurity Reduction: An Alternative to Conventional Chromatography for Monoclonal Antibody Purification," Biotechnol Bioeng 109(10):2589-2598 (2012).
Ma, J., et al., "Using precipitation by polyamines as an alternative to chromatographic separation in antibody purification processes," J Chromatogr B Analyt Technol Biomed Life Sci 878(9-10):798-806 (2010)(Abstract).
Li, L., et al., "Application of a PEG precipitation method for solubility screening: A tool for developing high protein concentration formulations," Protein Sci 22:1118-1123 (2013).
Capito, F., et al., "Host Cell Protein Quantification by Fourier Transform Mid Infrared Spectroscopy (FT-MIR)," Biotechnol Bioeng., 110:252-259 (2013).
Capito, F., "Matrix Effects During Monitoring of Antibody and Host Cell Proteins Using Attenuated Total Reflection Spectroscopy," Biotechnol Prog., 29:265-274 (2013).
Capito, F., et al., "Feasibility of polyelectrolyte-driven Fab fragment separation," Biotechnol J., 9:698-701 (2014).

(Continued)

*Primary Examiner* — Daniel E Kolker
*Assistant Examiner* — James L Rogers
(74) *Attorney, Agent, or Firm* — Nixon & Vanderhye P.C.

(57) ABSTRACT

A composition containing an antibody is prepared in such a state that the composition contains an anionic polymer at pH lower than the pI of the antibody, and impurities insolubilized by the anionic polymer are removed. More preferably, the composition is prepared in such a state that the composition contains an anionic polymer at pH lower than or equal to the pI of the antibody minus one, and impurities insolubilized by the anionic polymer are removed.

20 Claims, 5 Drawing Sheets
Specification includes a Sequence Listing.

(56) References Cited

OTHER PUBLICATIONS

Fahrner, R. L., et al., "Industrial Purification of Pharmaceutical Antibodies: Development, Operation, and Validation of Chromatography Processes," Biotechnol Genet Eng Rev., 18:301-327 (2001).

Fulton, A., et al., "Purification of monoclonal antibody against Ebola GP1 protein expressed in *Nicotiana benthamiana*," J Chromatogr A., 1389:128-132 (2015).

Anonymous, "Peptide—Wikipedia, the free encyclopedia," Wikipedia, the free encyclopedia, Jul. 12, 2016, pp. 1-5, XP055288608, retrieved from the Internet: URL:https://en.wikipedia.org/w/index.php?title=Peptide&printable=yes [retrieved on Jul. 14, 2016].

Anonymous, Sep. 8, 2020 Proteins/Biology for Non-Majors/Proteins/Biology for Non-Majors I, Aug. 19, 2020, pp. 1-12, XP55723932, retrieved from the Internet: URL:https://courses.lumenlearning.com/wmopen-nmbiology1/chapter/proteins/#:%7E:text=Prote%E2%80%A6 [retrieved on Aug. 20, 2020].

Dalkara, D., et al., "Intracytoplasmic Delivery of Anionic Proteins," Molecular Therapy, 9(6):964-969 (2004).

Kunugi, S., "Proteins as Polymers and Polyelectrolytes," Encyclopedia of Polymeric Nanomaterials, 6 pages (2014).

* cited by examiner

SEQUENCE LISTING

```
<160> NUMBER OF SEQ ID NOS: 6

<210> SEQ ID NO 1
<211> LENGTH: 443
<212> TYPE: PRT
<213> ORGANISM: Artificial Sequence
<220> FEATURE:
<223> OTHER INFORMATION: An artificially synthesized peptide sequence

<400> SEQUENCE: 1
```

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
            210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415
```

-continued

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 2
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 2

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 445
<212> TYPE: PRT
<213> ORGANISM: Artificial Sequence
<220> FEATURE:
<223> OTHER INFORMATION: An artificially synthesized peptide sequence

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445

<210> SEQ ID NO 4
<211> LENGTH: 214
<212> TYPE: PRT
<213> ORGANISM: Artificial Sequence
<220> FEATURE:

-continued

<223> OTHER INFORMATION: An artificially synthesized peptide sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 449
<212> TYPE: PRT
<213> ORGANISM: Artificial Sequence
<220> FEATURE:
<223> OTHER INFORMATION: An artificially synthesized peptide sequence

<400> SEQUENCE: 5

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 6
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30
```

-continued

```
Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

METHOD FOR PURIFYING COMPOSITION COMPRISING ANTIBODIES WITH ANIONIC POLYMER

CROSS-REFERENCE TO RELATED APPLICATIONS

This application is a U.S. National Phase of PCT Application No. PCT/JP2016/072270, filed Jul. 29, 2016, which claims the benefit of Japanese Patent Application No. 2015-151981, filed Jul. 31, 2015, each of which is incorporated herein by reference in its entirety.

REFERENCE TO SEQUENCE LISTING SUBMITTED ELECTRONICALLY

The content of the electronically submitted sequence listing (Name: 6663_0054_Sequence_Listing.txt; Size: 17.5 kilobytes; and Date of Creation: Dec. 6, 2017) filed with the application is incorporated herein by reference in its entirety.

TECHNICAL FIELD

The present invention relates to methods for purifying compositions comprising antibodies, methods for producing compositions comprising antibodies, methods for producing pharmaceutical compositions, and compositions comprising antibodies, using an anionic polymer.

BACKGROUND ART

With development of genetic recombination techniques, various protein formulations have become available in stable supply. Specifically, in recent years, various therapeutic antibodies with higher selectivity than that of conventional medicinal products have been developed by genetic recombination techniques and have entered clinical trials.

For drug products containing a biologically active protein produced by such genetic recombination techniques, it is necessary to remove impurities such as host cell-derived proteins (host cell proteins, hereinafter "HCP") and DNA, resin ligand fragments which are one of the raw materials in purification, and aggregates or fragments derived from the protein of interest. Currently, the World Health Organization (WHO) indicates that the acceptable amount of DNA in a biological medicinal product is 10 ng DNA/dose or less. Generally, to meet this criterion, impurities are removed by treating the aqueous cultured medium containing the bioactive protein obtained from the host cells with affinity chromatography, cation exchange chromatography, anion exchange chromatography, hydroxyapatite chromatography, or hydrophobic interaction chromatography, or a combination thereof. Furthermore, development of new purification ligands has advanced in recent years, and multimodal chromatography that has two functions of both the ion-exchanging action and hydrophobic interaction is also used for purification.

In particular, when the bioactive protein is an antibody that can be obtained by using mammalian cells as the host, the antibody is purified by treatment with the Protein A or Protein G affinity column chromatography by utilizing the property of Protein A or Protein G to bind to the Fc region of IgG, followed by various chromatography methods.

For example, in Japanese Patent Application Kohyo Publication No. (JP-A) H05-504579 (unexamined Japanese national phase publication corresponding to a non-Japanese international publication) (Patent Document 1), an antibody-containing aqueous cultured medium obtained from a mammalian cell culture was subjected to a protein A or protein G column chromatography to absorb the antibody to the column, the antibody was then eluted using an acidic solution (citric acid at a concentration of approximately 0.1 M at pH 3.0-3.5), and the resulting acidic eluate was purified by subsequent ion-exchange column chromatography and size exclusion column chromatography.

On the other hand, antibody purification using these column techniques had problems such as involving a high cost, requiring large-scale facilities, and being bottlenecked by the processing capacity of the column size. In particular, affinity column chromatography such as protein A or protein G column chromatography accounts for a large part of the cost required for antibody purification, and this had been a problem from the viewpoint of cost reduction.

Recently, antibody purification using a precipitation technique has been drawing attention as an alternative method to these conventional column techniques. Since the precipitation technique is a relatively simple protein purification technique that only changes the composition of a solution, it is expected to realize low-cost, high-capacity purification steps.

Antibody purification using a precipitation technique is, for example, described in WO2008/091740 (Patent Document 2). This document describes a method in which an anionic polymer is added to an antibody culture solution to precipitate the antibody, and then this antibody is collected by using a filter to remove impurities. As another embodiment, the document discloses a method in which a cationic polymer is added to precipitate impurities and then the impurities are removed by separation.

The method described by Yun Kang et al. (Non-patent Document 1) is another example. This document describes a method of using a cationic polymer to precipitate and remove impurities in an antibody solution.

CITATION LIST

Patent Documents

[Patent Document 1] JP-A (Kohyo) H05-504579
[Patent Document 2] WO2008/091740

Non-Patent Documents

[Non-Patent Document 1] Biotechnology and Bioengineering 110(11), P 2928, 2013

SUMMARY OF THE INVENTION

Problems to be Solved by the Invention

The method of precipitating the antibody itself using a precipitation technique as described in Patent Document 2 has a problem of lack of achievement of sufficient ability to remove HCP and DNA. Furthermore, there is the problem that the antibodies have to be separated and collected from a large amount of precipitates, and thus the collection using a filter is difficult. Furthermore, methods where impurities are precipitated using a cationic polymer as described in Patent Document 2 or Non-patent Document 1 do not always provide sufficient impurity removal rate. Furthermore, there have been no report on cases where impurity precipitation techniques that use cationic polymers are applied to antibodies with a low isoelectric point (hereinafter, referred to as "pI"). This would be because low-pI antibodies are easily precipitated by cationic polymers and the high yield and the impurity-removing ability cannot be accomplished at the same time.

Therefore, there is an expectation for methods for purifying antibodies that can substitute for conventional column chromatographic methods, in particular protein A column chromatography or protein G column chromatography, and achieve high ability to remove impurities by relatively simple techniques.

An objective of the present invention is to provide novel methods for purifying antibodies using precipitation technologies.

Means for Solving the Problems

As a result of dedicated research to achieve the above-mentioned objective, the present inventors discovered that high ability to remove both HCP and DNA can be achieved by adjusting pH of a composition comprising antibodies to a certain value in the antibody purification step, and precipitating and removing impurities using an anionic polymer. Surprisingly, the negatively charged anionic polymer was found to be able to remove and precipitate negatively charged DNA. Usually, an antibody is positively charged in a solution whose pH is adjusted to less than the pI of the antibody, and therefore it is expected that addition of an anionic polymer allows the antibody to precipitate through charge neutralization. However, the present inventors discovered that even when pH is adjusted to less than the pI of the antibody, impurities (HCP and DNA) can be precipitated and removed by an anionic polymer without precipitating the antibody from a composition comprising the antibody.

More specifically, the present invention provides [1] to [21] below:

[1] A method for purifying a composition comprising an antibody, which comprises the steps of:
 (a) preparing a composition comprising an antibody in such a state that the composition comprises an anionic polymer at pH lower than the pI of the antibody; and
 (b) removing an impurity insolubilized by the anionic polymer from the composition.
[2] The method of [1], wherein step (a) is preparing the composition in such a state that the composition comprises an anionic polymer at pH lower than or equal to the pI of the antibody minus one.
[3] The method of [1], wherein step (a) is preparing the composition in such a state that the composition comprises an anionic polymer at pH of 3.5 to less than the pI of the antibody.
[4] The method of [1], wherein step (a) is preparing the composition in such a state that the composition comprises an anionic polymer at pH of 3.5 to the pI of the antibody minus one or lower.
[5] A method for purifying a composition comprising an antibody, which comprises the steps of:
 (a) preparing a composition comprising an antibody in such a state that the composition comprises an anionic polymer at pH of 3.5 to 5.0; and
 (b) removing an impurity insolubilized by the anionic polymer from the composition.
[6] The method of [5], wherein step (a) is preparing the composition in such a state that the composition comprises an anionic polymer at pH of 3.8 to 5.0.
[7] The method of any one of [1] to [6], wherein the pI of the antibody is 3.0 to 8.0.
[8] The method of any one of [1] to [6], wherein the pI of the antibody is 5.0 to 7.0.

[9] The method of any one of [1] to [8], wherein the anionic polymer is polyvinylsulfonic acid (PVS), polyacrylic acid (PAA), or polystyrenesulfonic acid (PSS).
[10] The method of any one of [1] to [9], wherein step (b) is removing an impurity insolubilized by an anionic polymer using a filter.
[11] The method of any one of [1] to [10], wherein the antibody has been produced in a CHO cell.
[12] The method of any one of [1] to [11], wherein the antibody is a monoclonal antibody and is a humanized antibody or a human antibody.
[13] The method of [12], wherein the antibody is an anti-tissue factor antibody, anti-IL-6 receptor antibody, anti-IL-6 antibody, anti-HM1.24 antigen monoclonal antibody, anti-parathyroid hormone-related peptide antibody (anti-PTHrP antibody), anti-glypican-3 antibody, anti-ganglio-side GM3 antibody, anti-TPO receptor agonist antibody, antibody functionally substituting for coagulation factor VIII, anti-IL31 receptor antibody, anti-HLA antibody, anti-AXL antibody, anti-CXCR4 antibody, anti-NR10 antibody, or bispecific antibody against factor IX or factor IXA and factor X.
[14] The method of any one of [1] to [13], wherein the impurity is a host cell-derived protein (HCP) and/or a DNA.
[15] A method for removing an impurity from an antibody-producing cell culture fluid (HCCF) using the method of any one of [1] to [14].
[16] The method of [15], wherein the anionic polymer is polyvinylsulfonic acid (PVS) and step (a) is preparing the composition in such a state that the composition comprises polyvinylsulfonic acid (PVS) at a mass ratio of 0.01 to 0.1 to the antibody.
[17] A method for removing an impurity from a protein A elution fraction or protein G elution fraction using the method of any one of [1] to [14], wherein the protein A elution fraction or protein G elution fraction is a product purified from an antibody-producing cell culture fluid (HCCF) by protein A column chromatography and/or protein G column chromatography.
[18] The method of any one of [15] to [17], which further comprises a purification step that uses any one or a combination of anion exchange column chromatography, cation exchange column chromatography, hydrophobic interaction column chromatography, and multimode chromatography.
[19] A method for producing a composition comprising an antibody in which the mass ratio of an impurity to the antibody has been lowered to 0.2 or less, wherein the method comprises removing the impurity by the method of any one of [1] to [16], and does not comprise a purification step using protein A column chromatography and/or protein G column chromatography.
[20] A method for producing a pharmaceutical composition, which comprises producing a composition comprising an antibody by the method of [19], and formulating said composition by admixing the composition with a pharmaceutically acceptable carrier and/or additive.
[21 A composition comprising an antibody, which
 is produced by the method of any one of [1] to [16],
 comprises an antibody whose pI is 5.0 to 7.0,
 has a mass ratio of impurity content to the antibody that is 0.2 or less, and
 does not comprise protein A and/or protein G as the impurity.

Effects of the Invention

The present invention provides novel antibody purification methods that can substitute for conventional column chromatography.

MODE FOR CARRYING OUT THE INVENTION

Figure 1:
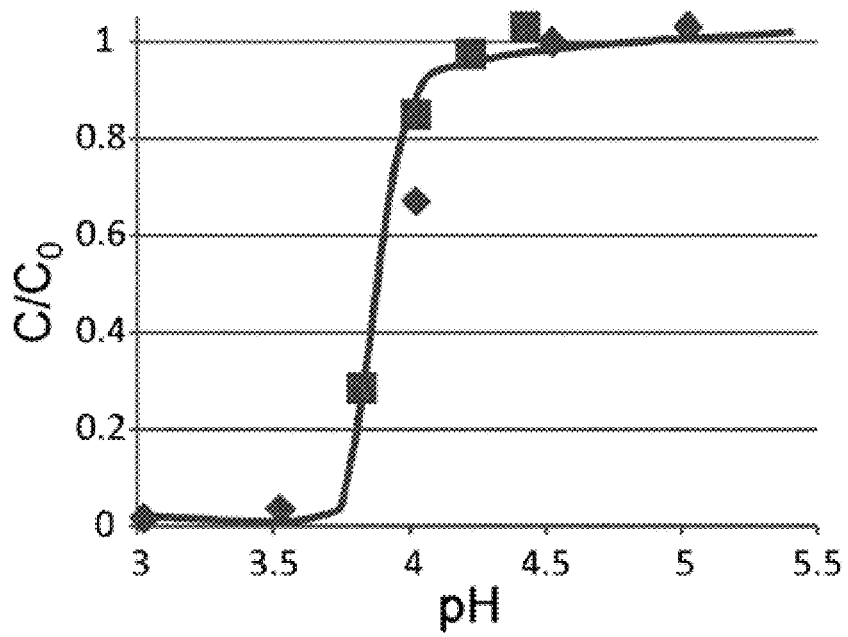
FIG. 1 shows a graph indicating the yield of antibodies at each pH value. C/Co on the vertical axis shows the ratio of Mab1 before and after removing impurities by precipitation using an anionic polymer.

Herein below, the present invention will be specifically described.

The present invention relates to methods for removing impurities from a composition comprising an antibody by using an anionic polymer. Specifically, the present invention relates to a method for purifying a composition comprising an antibody, which comprises the steps of:
  (a) preparing a composition comprising an antibody in such a state that the composition comprises an anionic polymer at pH lower than the pI of the antibody; and
  (b) removing an impurity insolubilized by the anionic polymer from the composition.

Producing a state in which an anionic polymer is contained at pH lower than the pI of the antibody in step (a) is accomplished, for example, by adjusting pH of the antibody-containing solution to a desired value at room temperature, then adding an anionic polymer, and then stirring the composition so that the anionic polymer therein becomes substantially homogeneous. To stir the composition, for example, but without limitations, a stir bar can be used to stir it for a certain amount of time. The duration for stirring may be, for example, but not limited to, five minutes to one hour, or preferably 15 minutes to 30 minutes. pH adjustment can be carried out after addition of the anionic polymer to the composition, or both before and after the anionic polymer addition. Particularly, when adding a relatively large amount of anionic polymer, pH before and after the anionic polymer addition may change. In such a case, it is effective to perform pH adjustment and stirring both before and after the addition.

Therefore, in a detailed example, step (a) can include the following steps:
  (a1) adjusting pH of a composition comprising an antibody to lower than the pI of the antibody;
  (a2) adding an anionic polymer to the composition; and
  (a3) stirring the composition to make the anionic polymer in the composition substantially homogeneous.

In the present invention, it is not required that the anionic polymer in the composition be completely homogeneous. In the present invention, "substantially homogeneous" means a state in which sufficient degree of homogeneity is ensured for insolubilizing impurities by the anionic polymer.

Furthermore, in the present invention, "adding" can be reworded as "admixing".

Therefore, in the present invention, an antibody-containing solution comprising an anionic polymer can be prepared by admixing an antibody-containing solution with an anionic polymer.

The methods for adjusting pH of a composition comprising an antibody, or specifically, adjusting it to produce an acidic condition, includes methods of adding known acids such as hydrochloric acid, citric acid, phosphoric acid, and acetic acid. Methods for adjusting pH of the composition to an alkaline condition similarly includes adding known bases. As described above, there are countless means for performing step (a), and as long as pH of the anionic polymer is adjusted to the desired value in the composition comprising an antibody, the means are not particularly limited.

In the present invention, when an anionic polymer is contained, pH of the composition is adjusted to a value lower than the pI of the antibody. Examples include, but are not limited, values that are lower than the pI of the antibody, and differ from the pI of the antibody by 3 or less (for example, 3.0, 2.9, 2.8, 2.7, 2.6, 2.5, 2.4, 2.3, 2.2, 2.1 or less), 2 or less (for example, 2.0, 1.9, 1.8, 1.7, 1.6, 1.5, 1.4, 1.3, 1.2, 1.1 or less), or 1 or less (for example, 1.0, 0.9, 0.8, 0.7, 0.6, 0.5, 0.4, 0.3, 0.2, 0.1 or less).

As described below, preferably the pH value can be adjusted to a value lower than or equal to pI-1 (pI minus one), or a value of 3.5 to less than the pI of the antibody, and even more preferably, it can be adjusted to 3.5 to lower than or equal to the pI of the antibody minus one. Furthermore, the pH value can be adjusted to 3.5 to 5.0, or more preferably 3.8 to 5.0. In the present invention, a value "lower than or equal to pI minus one" preferably refers to a value not more than "a value within the range of a value equal to pI to a value of pI minus one", and more preferably refers to a value not more than "a value of pI minus one".

In the present invention, an anionic polymer can be used singularly or in the form of a composition or a solution. Examples of anionic polymers used in the present invention include, but are not particularly limited to, polyvinylsulfonic acid (hereinafter, "PVS"), polyacrylic acid (hereinafter, "PAA"), and polystyrenesulfonic acid (hereinafter, "PSS"), or a mixture or a combination thereof.

When using PVS as an anionic polymer, its degree of polymerization, molecular weight, and whether its structure is a linear chain or branched chain do not matter. Methods for synthesizing such anionic polymers are well known to those skilled in the art. Alternatively, these anionic polymers can be obtained through a supplier.

In the present invention, the amount of anionic polymer admixed with an antibody-comprising composition can be represented as a ratio between the antibody mass and the anionic polymer mass ($g_{polymer}/g_{antibody}$). For example, when precipitating impurities present in an antibody-producing cell culture fluid (HCCF) using PVS, the mass ratio can be set to 0.01 to 0.1.

In the present invention, the removal of impurities insolubilized by the anionic polymer in step (b) above can be carried out by performing filtration with, for example, a polyethersulfone (hereinafter "PES") filter using a method well known to those skilled in the art. When the amount of precipitation is large, a Grassfiber filter may be used. Alternatively, when the scale of production or such is large, a Depth filter may be used. The material used for the Depth filter may be glass fiber, cellulose, polyvinylidene fluoride (PVDF), or such, without being limited thereto. Alternatively, in the present invention, a method that uses centrifugation may be used instead of the method of removal using a filter. In the present invention, the step of collecting antibodies can be included after the step of removing impurities insolubilized by an anionic polymer.

The impurity to be removed in the present invention may be any substance as long as it is not the antibody of interest. Examples of the impurity include, but are not limited to, HCP and DNA, substances eluted from Protein A column chromatography, fragments and aggregates derived from the protein of interest, viruses, endotoxins, protein hydrolysates which are medium components, IGF, insulin, antibiotics, and anti-foaming agents. Particularly, in the Examples of the present invention, compositions comprising antibodies produced by CHO host cells are used to evaluate the removal rates of HCP and DNA derived from the host cells.

In the case where impurities are antibodies of different sizes (dimer, trimer, half-mer, etc.), whether the impurities have been removed can be determined by performing size exclusion chromatography (SEC), without limitation thereto.

In the case of DNA contaminant, the determination can be carried out by a qPCR method, a threshold method, or such, without limitation thereto.

In the case of a cell-derived protein (host cell protein/HCP), the determination can be carried out by ELISA that uses anti-HCP antibodies, without limitation thereto.

In the case of Protein A, the determination can be carried out by ELISA that uses anti-Protein A antibodies, without limitation thereto.

In the case of viruses, the determination can be carried out by a qPCR method, tissue infection method, plaque method, or such, without limitation thereto.

In the case of IGF, the determination can be carried out by ELISA that uses anti-IGF antibodies, without limitation thereto.

In the case of insulin, the determination can be carried out by ELISA that uses anti-insulin antibodies, without limitation thereto.

In the case of protein hydrolysates, the determination can be carried out by ELISA that uses anti-protein hydrolysate antibodies, without limitation thereto.

In the case of anti-foaming agents, the determination can be carried out by NMR, without limitation thereto.

In the case of endotoxin, the determination can be carried out by a colorimetric method or turbidimetry based on the reaction that activates limulus amebocyte lysate (LAL) which is a component extracted from blood cells of horseshoe crab, without limitation thereto.

In the case of antibiotics, their concentrations can be determined by ELISA that uses antibodies which specifically recognize antibiotics such as gentamycin, without limitation thereto.

In the present invention, "composition comprising an antibody" refers to a composition before, after, or during application of the impurity removing method of the present invention. The composition comprising an antibody can be rephrased as an antibody-containing solution, an antibody-producing cell culture fluid (harvested cell culture fluid, hereinafter "HCCF"), an antibody-producing cell culture medium, or such. It can be a culture fluid obtained after applying a purification step using a conventional column chromatography technique to HCCF, and for example, it may be a protein A elution fraction. In the present invention, prior to filtration, a composition comprising antibodies can be subjected to centrifugation, and the obtained supernatant can be subjected to filtration.

Antibodies used in the present invention are not particularly limited as long as they bind to the desired antigens. While they may be polyclonal antibodies or monoclonal antibodies, monoclonal antibodies are preferred in that homogeneous antibodies can be stably produced. Furthermore, since antibody pI is taken into consideration when adjusting pH of the composition in the present invention, a monoclonal antibody whose pI value can be determined easily is preferred.

The antibodies used in the present invention include not only those derived from animals such as humans, mice, rats, hamsters, rabbits, sheep, camels, and monkeys, but also artificially engineered recombinant antibodies such as chimeric antibodies, humanized antibodies, human antibodies, and bispecific antibodies, and antibody-like molecules. These antibodies also include recombinant antibodies produced by artificially engineering the antibody constant regions and such to alter the physical properties of the antibody molecule (specifically, alteration of the isoelectric point (pI), alteration of the Fc receptor affinity, etc.) for the purpose of improving blood retention or in vivo kinetics.

The immunoglobulin class of the antibodies used in the present invention is not particularly limited, and the class may be any class, including IgG such as IgG1, IgG2, IgG3, and IgG4, IgA, IgD, IgE, and IgM. However, IgG and IgM are preferred.

The antibodies used in the present invention also include not only antibodies that have constant regions and variable regions (whole antibodies) but also antibody fragments such as Fv, Fab, and F(ab)$_2$, and low-molecular-weight antibodies (minibodies) such as mono-, bi-, or multi-valent single-chain Fv (scFv, sc(Fv)$_2$) that result from linking antibody variable regions via a linker such as peptide linker, and diabodies such as scFv dimer; however, whole antibodies are preferred.

The above-described antibodies used in the present invention can be prepared by methods known to those skilled in the art. Basically, monoclonal antibody-producing hybridomas can be prepared by using known techniques such as those described below. More specifically, immunization is carried out by a conventional immunization method using a desired antigen or cells expressing the desired antigen as a sensitizing antigen. The resulting immune cells are fused with known parental cells by a conventional cell fusion method. The fused cells are screened for monoclonal antibody-producing cells (hybridomas) by conventional screening methods to produce the antibodies. Hybridomas can be generated, for example, according to the method of Milstein et al. (Kohler, G. and Milstein, C., Methods Enzymol. (1981) 73: 3-46). When an antigen has low immunogenicity, immunization can be performed by linking the antigen to an immunogenic macromolecule such as albumin.

Alternatively, it is possible to use recombinant antibodies produced using gene recombination techniques in which antibody genes are cloned from hybridomas and inserted into appropriate vectors, and the resulting vectors are introduced into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs for antibody variable regions (V regions) are synthesized from mRNAs of the hybridomas using reverse transcriptase. When a DNA encoding an antibody V region of interest is obtained, the DNA is linked to a DNA encoding a desired antibody constant region (C region). The resulting construct is inserted into an expression vector. Alternatively, the antibody V region-encoding DNA may be inserted into an expression vector carrying the DNA of the antibody C region. The resulting construct is inserted into an expression vector so that it is expressed under the control of an expression regulatory region, for example, an enhancer or a promoter. Then, host cells are transformed with the expression vector to express the antibody.

In the present invention, artificially modified recombinant antibodies, for example, chimeric and humanized antibodies can be used to reduce heterologous antigenicity against humans, and such. Such modified antibodies can be produced using known methods. A chimeric antibody is an antibody consisting of the heavy-chain and light-chain variable regions of an antibody from a non-human mammal such as mouse, and the heavy-chain and light-chain constant regions of a human antibody. The chimeric antibody can be obtained by linking a DNA encoding the variable regions of a mouse antibody to a DNA encoding the constant regions of a human antibody, inserting it into an expression vector, and then introducing the vector into a host to produce the antibody.

A humanized antibody is also referred to as a reshaped human antibody, and is obtained by transplanting the complementarity determining region (CDR) of an antibody derived from a non-human mammal such as mouse into the complementarity determining region of a human antibody. Its general gene recombination techniques are known. Specifically, a DNA sequence is designed to have a mouse antibody CDR linked to a human antibody framework region (FR), and is synthesized by PCR using several oligonucleotides prepared to have overlapping portions at their ends. The obtained DNA is ligated to a DNA encoding a human antibody constant region and then inserted into an expression vector. The expression vector is introduced into a host to produce the humanized antibody (see European Patent Application Publication No. EP 239400 and WO 96/02576). The CDR-linked human antibody FR is selected so that the complementarity determining region forms a preferable antigen-binding site. Amino acids in the framework region of the antibody variable region can be substituted as required so that the complementarity determining region of the reshaped human antibody forms a suitable antigen-binding site (Sato, K. et al., Cancer Res. (1993) 53, 851-856).

Techniques for substituting amino acid(s) in an antibody to increase activities, physical properties, pharmacokinetics, safety, and such of the antibody are known, and examples of such techniques are described below. The antibodies used in the present invention also include those having such amino acid substitutions (and including also deletions and additions).

Techniques have been reported for substituting amino acid(s) in the IgG antibody variable regions, and include humanization (Tsurushita N, Hinton P R, Kumar S., Design of humanized antibodies: from anti-Tac to Zenapax., Methods. 2005 May; 36(1): 69-83); affinity maturation to enhance the binding activity via amino acid substitution in the complementarity determining region (CDR) (Rajpal A, Beyaz N, Haber L, Cappuccilli G, Yee H, Bhatt R R, Takeuchi T, Lerner R A, Crea R., A general method for greatly improving the affinity of antibodies by using combinatorial libraries., Proc Natl Acad Sci USA. 2005 Jun. 14; 102(24): 8466-71); and improvement of physicochemical stability via amino acid substitution in the framework (FR) (Ewert S, Honegger A, Pluckthun A., Stability improvement of antibodies for extracellular and intracellular applications: CDR grafting to stable frameworks and structure-based framework engineering., Methods. 2004 October; 34(2): 184-99. Review). There are also known techniques for enhancing antibody-dependent cellular cytotoxicity (ADCC) and complement-dependent cytotoxicity (CDC) by substituting amino acid(s) in the IgG antibody Fc region (Kim S J, Park Y, Hong H J., Antibody engineering for the development of therapeutic antibodies., Mol Cells. 2005 Aug. 31; 20(1): 17-29. Review). Furthermore, in addition to such techniques for enhancing effector functions, there are reports on techniques for increasing the antibody half-life in blood by substituting amino acid(s) in Fc (Hinton P R, Xiong J M, Johlfs M G, Tang M T, Keller S, Tsurushita N., An engineered human IgG1 antibody with longer serum half-life., J Immunol. 2006 Jan. 1; 176(1): 346-56; Ghetie V, Popov S, Borvak J, Radu C, Matesoi D, Medesan C, Ober R J, Ward E S., Increasing the serum persistence of an IgG fragment by random mutagenesis., Nat. Biotechnol. 1997 July; 15(7): 637-40). Various techniques of substituting amino acid(s) in the constant regions for the purpose of increasing the physical properties of an antibody are also known (WO 09/41613).

Methods for obtaining human antibodies are also known. For example, desired human antibodies with antigen-binding activity can be obtained by sensitizing human lymphocytes in vitro with an antigen of interest or with cells expressing an antigen of interest; and fusing the sensitized lymphocytes with human myeloma cells such as U266 (see Japanese Patent Application Kokoku Publication No. (JP-B) H01-59878 (examined, approved Japanese patent application published for opposition)). Alternatively, desired human antibodies can also be obtained by immunizing transgenic animals having the entire repertoire of human antibody genes with an antigen (see WO 93/12227, WO 92/03918, WO 94/02602, WO 94/25585, WO 96/34096, and WO 96/33735). Furthermore, techniques for obtaining human antibodies by panning with a human antibody library are known. For example, the variable regions of human antibodies are expressed as single-chain antibodies (scFvs) on the surface of phages using a phage display method, and then phages that bind to the antigen can be selected. Genes of the selected phages can be analyzed to determine DNA sequences that encode the variable regions of the human antibodies that bind to the antigen. When the DNA sequences of scFvs that bind to the antigen are identified, appropriate expression vectors carrying these sequences can be constructed to obtain human antibodies. Such methods are already well known, and WO 92/01047, WO 92/20791, WO 93/06213, WO 93/11236, WO 93/19172, WO 95/01438, and WO 95/15388 can be used as reference. The antibodies used in the present invention also include such human antibodies.

When an antibody gene is isolated and then introduced into appropriate hosts to produce antibodies, hosts and expression vectors can be used in appropriate combinations. When eukaryotic cells are used as the host, animal cells, plant cells, and fungal cells can be used. Known animal cells include: (1) mammalian cells, for example, CHO, COS, myeloma, baby hamster kidney (BHK), HeLa, and Vero; (2) amphibian cells, for example, *Xenopus* oocytes; and (3) insect cells, for example, sf9, sf21, and Tn5. Known plant cells include cells derived from the genus *Nicotiana* such as *Nicotiana tabacum*, which can be cultured as a callus. Known fungal cells include yeasts such as the genus *Saccharomyces*, for example, *Saccharomyces cerevisiae*, and filamentous fungi such as the genus *Aspergillus*, for example, *Aspergillus niger*. When using prokaryotic cells, production systems using bacterial cells can be used. Known bacterial cells include *Escherichia coli* (*E. coli*) and *Bacillus subtilis*. Antibodies can be obtained by introducing the antibody genes of interest into these cells by transformation and then culturing the transformed cells in vitro.

The antibodies used in the present invention also include antibody fragments, minibodies, and antibody modification products. Antibody fragments and minibodies include, for example, Fab, F(ab')2, Fv, or mono-, bi-, or multi-valent single-chain Fv (scFv, sc(Fv)$_2$, or such) that result from linking the H chain and L chain Fvs via appropriate linkers (Huston J. S. et al., Proc. Natl. Acad. Sci. U.S.A. (1988) 85: 5879-5883). Specifically, such antibody fragments are generated by treating antibodies with an enzyme such as papain or pepsin. Alternatively, genes encoding these antibody fragments are constructed, inserted into expression vectors, and then expressed in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Antibodies linked to various molecules such as polyethylene glycol (PEG) or cytotoxic agents may be used as antibody modification products (Farmaco. 1999 Aug. 30; 54(8): 497-516; Cancer J. 2008 May-June; 14(3): 154-69). The antibodies used in the present invention also include such antibody modification products. Such antibody modification products can be obtained by chemically modifying antibodies. Such methods are already established in this field.

For example, an antibody having an activity can be efficiently prepared by using the purification method according to the present invention. Examples of the activity can include binding activity, neutralizing activity, cytotoxic activity, agonistic activity, antagonistic activity, and enzymatic activity. The agonistic activity is an activity of inducing change in some physiological activity due to, for example, the binding of an antibody to an antigen such as a receptor to intracellularly transduce signals. Examples of the physiological activity can include, but are not limited to, proliferative activity, survival activity, differentiation activity, transcriptional activity, membrane transport activity, binding activity, proteolytic activity, phosphorylating/dephosphorylating activity, redox activity, transfer activity, nucleolytic activity, dehydration activity, cell death-inducing activity, and apoptosis-inducing activity.

Furthermore, an antibody that recognizes a desired antigen or binds to a desired antigen can be efficiently obtained by the purification method of the present invention. Herein, the antigen is not particularly limited, and can be any antigen. Preferred examples of the antigen include ligands (cytokines, chemokines, etc.), receptors, cancer antigens, MHC antigens, differentiation antigens, immunoglobulins, and immunocomplexes partially containing an immunoglobulin.

Examples of the cytokines can include interleukins 1 to 18, colony-stimulating factors (G-CSF, M-CSF, GM-CSF, etc.), interferons (IFN-α, IFN-β, IFN-γ, etc.), growth factors (EGF, FGF, IGF, NGF, PDGF, TGF, HGF, etc.), tumor necrosis factors (TNF-α and TNF-β), lymphotoxin, erythropoietin, leptin, SCF, TPO, MCAF, and BMP.

Examples of the chemokines can include CC chemokines such as CCL1 to CCL28, CXC chemokines such as CXCL1 to CXCL17, C chemokines such as XCL1 to XCL2, and CX3C chemokines such as CX3CL1.

Examples of the receptors can include receptors belonging to receptor families such as hematopoietic factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. The receptors belonging to these receptor families and their features are described in many documents, for example, Cooke B A., King R J B., van der Molen H J, ed. New Comprehensive Biochemistry Vol. 18B "Hormones and their Actions Part II" pp. 1-46 (1988) Elsevier Science Publishers BV., Patthy (Cell (1990) 61 (1), 13-14), Ullrich et al. (Cell (1990) 61 (2), 203-212), Massague (Cell (1992) 69 (6), 1067-1070), Miyajima et al. (Annu. Rev. Immunol. (1992) 10, 295-331), Taga et al. (FASEB J. (1992) 6, 3387-3396), Fantl et al. (Annu. Rev. Biochem. (1993), 62, 453-481), Smith et al. (Cell (1994) 76 (6) 959-962), and Flower D R. (Biochim. Biophys. Acta (1999) 1422 (3) 207-234).

Preferred examples of specific receptors belonging to the above-mentioned receptor families include human or mouse erythropoietin (EPO) receptors (Blood (1990) 76 (1), 31-35; and Cell (1989) 57 (2), 277-285), human or mouse granulocyte colony-stimulating factor (G-CSF) receptors (Proc. Natl. Acad. Sci. USA. (1990) 87 (22), 8702-8706; mG-CSFR; and Cell (1990) 61 (2), 341-350), human or mouse thrombopoietin (TPO) receptors (Proc Natl Acad Sci USA. (1992) 89 (12), 5640-5644; and EMBO J. (1993) 12 (7), 2645-53), human or mouse insulin receptors (Nature (1985) 313 (6005), 756-761), human or mouse Flt-3 ligand receptors (Proc. Natl. Acad. Sci. USA. (1994) 91 (2), 459-463), human or mouse platelet-derived growth factor (PDGF) receptors (Proc. Natl. Acad. Sci. USA. (1988) 85 (10) 3435-3439), human or mouse interferon (IFN)-α/β receptors (Cell (1990) 60 (2), 225-234; and Cell (1994) 77 (3), 391-400), human or mouse leptin receptors, human or mouse growth hormone (GH) receptors, human or mouse interleukin (IL)-10 receptors, human or mouse insulin-like growth factor (IGF)-1 receptors, human or mouse leukemia inhibitory factor (LIF) receptors, and human or mouse ciliary neurotrophic factor (CNTF) receptors.

Cancer antigens are expressed with the malignant transformation of cells, and are also called tumor-specific antigens. Abnormal sugar chains that appear on cell surface or protein molecules when cells are cancerated are also included in the cancer antigens and are also called cancer carbohydrate antigens. Preferred examples of the cancer antigens include GPC3 that belongs to the GPI-anchored receptor family as the aforementioned receptors and is expressed in some cancers including liver cancer (Int J Cancer. (2003) 103 (4), 455-65), EpCAM that is expressed in a plurality of cancers including lung cancer (Proc Natl Acad Sci USA. (1989) 86 (1), 27-31), CA19-9, CA15-3, and sialyl SSEA-1 (SLX).

The MHC antigens are mainly classified into MHC class I antigens and MHC class II antigens. The MHC class I antigens include HLA-A, -B, -C, -E, -F, -G, and -H. The MHC class II antigens include HLA-DR, -DQ, and -DP.

The differentiation antigens can include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

Antibodies to be used in the present invention include, but are not limited to, anti-tissue factor antibodies, anti-IL-6 receptor antibodies, anti-IL-6 antibodies, anti-HM1.24 antigen monoclonal antibodies, anti-parathyroid hormone-related peptide antibodies (anti-PTHrP antibodies), anti-glypican-3 antibodies, anti-ganglioside GM3 antibodies, anti-TPO receptor agonist antibodies, antibodies functionally substituting for coagulation factor VIII, anti-IL31 receptor antibodies, anti-HLA antibodies, anti-AXL antibodies, anti-CXCR4 antibodies, anti-NR10 antibodies, and bispecific antibodies against factor IX or factor IXa and factor X.

Preferred reshaped humanized antibodies used in the present invention include, but are not limited to humanized anti-interleukin 6 (IL-6) receptor antibodies (tocilizumab, hPM-1, or MRA) (see WO 92/19759), humanized anti-HM1.24 antigen monoclonal antibodies (see WO 98/14580), humanized anti-parathyroid hormone-related peptide antibodies (anti-PTHrP antibodies) (see WO 98/13388), humanized anti-tissue factor antibodies (see WO 99/51743), anti-glypican-3 humanized IgG1K antibodies (see PCT/JP05/013103), anti-NR10 humanized antibodies (see WO 2009/072604), and bi-specific humanized antibodies against factor IX or factor IXa and factor X.

Preferred human IgM antibodies include anti-ganglioside GM3 recombinant human IgM antibodies (see WO 05/05636).

Preferred minibodies include anti-TPO receptor agonist diabodies (see WO 02/33072) and anti-CD47 agonist diabodies (see WO 01/66737).

Purification methods of the present invention are expected to be more highly effective for low-pI antibodies such as humanized anti-IL-6 receptor antibodies, anti-NR10 humanized antibodies, and bispecific humanized antibodies against factor IX or factor IXa and factor X. This is because, with low-pI antibodies, it is easier to find out the optimal pH value that yields conditions with high precipitation rates of impurities and low precipitation rates of antibodies as described in detail below in the Examples.

In the present invention, antibodies with a low pI (hereinafter, "low-pI antibodies") refers particularly to antibodies that have a low isoelectric point, which hardly exist in nature. The isoelectric points of such antibodies may be, for example 3.0 to 8.0, preferably 5.0 to 7.0, more preferably 5.5 to 7.0, and particularly preferably 5.6 to 6.9 and 5.6 to 5.8, but are not limited thereto. Native (or ordinary) antibodies are thought to usually have an isoelectric point in the range of 7.5 to 9.5.

Furthermore, preferred antibodies to be used in the present invention include pI-modified antibodies in which the amino acid residue(s) exposed on the antibody surface is/are modified to lower the pI of the antibodies. The pI-modified antibody refers to an antibody whose pI has been lowered by 1 or more, preferably 2 or more, and more preferably 3 or more compared to the pI of the antibody before the modification. As described below, pI (theoretical isoelectric point) of Mab1 used in Examples 1 and 2 was 5.6, pI (theoretical isoelectric point) of Mab2 used in Examples 3 and 4 was 5.8, and pI (theoretical isoelectric point) of Mab3 used in Example 5 was 6.9.

In the case of an H-chain variable region, examples of amino acid residues exposed on the antibody surface include amino acid residues selected from among the amino acid residues at H1, H3, H5, H8, H10, H12, H13, H15, H16, H19, H23, H25, H26, H31, H39, H42, H43, H44, H46, H61, H62, H64, H65, H68, H71, H72, H73, H75, H76, H81, H82b, H83, H85, H86, H97, H105, H108, H110, and H112 according to Kabat numbering, but are not limited thereto. In the case of an L-chain variable region, the examples are amino acid residues selected from among the amino acid residues at L1, L3, L7, L8, L9, L11, L12, L16, L17, L18, L20, L22, L24, L27, L38, L39, L41, L42, L43, L45, L46, L49, L53, L54, L55, L57, L60, L63, L65, L66, L68, L69, L70, L74, L76, L77, L79, L80, L81, L85, L100, L103, L105, L106, and L107 according to Kabat numbering, but are not limited thereto.

In the present invention, "modification" refers to substituting the original amino acid residue with another amino acid residue, deleting the original amino acid residue, adding a new amino acid residue, and such, but preferably, it refers to substitution of the original amino acid residue with another amino acid residue.

Some amino acids are known to be charged amino acids. Generally, lysine (K), arginine (R), and histidine (H) are known as positively charged amino acids (cationic amino acids). Aspartic acid (D), glutamic acid (E), and such are known as negatively charged amino acids (anionic amino acids). Amino acids other than these are known as uncharged amino acids.

In the present invention, preferably, the amino acid residues present after the modification are suitably selected from the amino acid residues included in either one of groups (a) and (b) below, without particular limitations thereto:

(a) glutamic acid (E) and aspartic acid (D); and
(b) lysine (K), arginine (R), and histidine (H).

In a preferred embodiment, if the amino acid residue before modification is already charged, it may be modified to be an uncharged amino acid residue.

More specifically, the modification in the present invention includes: (1) substitution of a charged amino acid with an uncharged amino acid; (2) substitution of a charged amino acid with an amino acid carrying a charge opposite to that of the original amino acid; and (3) substitution of an uncharged amino acid with a charged amino acid.

The pI value can be determined by isoelectric focusing known to those skilled in the art. Theoretical isoelectric point values can be calculated using a gene or amino acid sequence analysis software (for example, Genetyx).

Antibodies in which the charge of amino acid residues has been modified can be obtained by modifying nucleic acids encoding the antibodies, culturing those nucleic acids in host cells, and purifying the antibodies from the host cell culture. In the present invention, the phrase "modifying nucleic acids" refers to modifying nucleic acid sequences so that they become codons that correspond to amino acid residues introduced by the modification. More specifically, it refers to modifying the nucleotide sequence of a nucleic acid so that the codon encoding the original amino acid residue becomes a codon encoding the amino acid residue to be introduced by the modification. That is, a codon encoding the amino acid residue to be modified is replaced by a codon encoding the amino acid residue to be introduced by the modification. Such nucleic acid modifications can be carried out appropriately by those skilled in the art using known techniques, for example, site-directed mutagenesis or PCR mutagenesis.

The purification methods of the present invention can be used in place of a purification method that uses a column chromatography technique, or in combination with a purification method that uses a column chromatography technique. Specifically, a purification method that uses an anionic polymer can be applied to an antibody-producing cell culture fluid (HCCF). In this case, the purification step that uses an anionic polymer of this invention can be substituted for a conventional purification step that uses protein A column chromatography and/or protein G column chromatography, and this will enable purification to be performed without the use of such column chromatography.

In another method, it is possible to apply the purification method that uses an anionic polymer to a protein A elution fraction or a protein G elution fraction obtained by purifying an antibody-producing cell culture fluid (HCCF) by protein A column chromatography and/or protein G column chromatography. The order in which the purification by protein A column chromatography and/or protein G column chromatography and the purification by an anionic polymer are carried out can be changed as appropriate. Preferably, the purification step using an anionic polymer can be substituted for any of the plurality of purification steps that use polishing column chromatography.

In the present invention, for example, Mab Select SuRe (GE Healthcare) can be used for protein A column chromatography, and Protein G Sepharose 4 Fast Flow (GE Healthcare) can be used for protein G column chromatography.

Polishing column chromatography is defined as column chromatography used for intermediate purification and polishing steps. The intermediate purification step and the polishing step refer to the Protein A and Protein G column chromatography step and the column chromatography step after the capture step of column chromatography. An example of the polishing column chromatography is any one or any combination of anion exchange column chromatography, cation exchange column chromatography, hydrophobic interaction column chromatography, and multimodal chromatography, but is not limited thereto.

In the present invention, the anion exchange column is not limited as long as it shows an anion exchange action, and examples include:
YMC-BioPro (YMC Co. Ltd);
Q Sepharose High Performance (GE Healthcare);
Q Sepharose Fast Flow (GE Healthcare);
Q Sepharose XL (GE Healthcare);
Capto Q ImpRes (GE Healthcare);
Capto Q (GE Healthcare);
Capto DEAE (GE Healthcare);
SOURCE 30Q (GE Healthcare);
SOURCE 15Q (GE Healthcare);
POROS HQ (Life technologies, Inc.);
POROS D (Life technologies, Inc.);
POROSPI (Life technologies, Inc.);
Eshumuno Q (Merck Millipore Corp.);
Fractogel TMAE (Merck Millipore Corp.);
Fractogel DEAE (Merck Millipore Corp.);
Macro-Prep Q (Bio-Rad Laboratories Inc.);
Macro-Prep DEAE (Bio-Rad Laboratories Inc.);
Giga Cap Q-650M (TOSOH Corp.);
Giga Cap DEAE-650M (TOSOH Corp.); and
Q HyperCel (PALL Corp.).

In the present invention, the cation exchange column is not limited as long as it shows a cation exchange action, and examples include:
POROS 50HS (Applied Biosystem);
POROS XS (Applied Biosystem);
Eshumuno S (Merk-Millipore);
Fractogel SO3- (M) (Merk-Millipore);
Fractogel COO— (M) (Merk-Millipore);
Fractogel SO3- (S) (Merk-Millipore);
Fractogel COO— (S) (Merk-Millipore);
MacroPrep High S (Bio-Rad);
MacroPrep CM (Bio-Rad);
UNO sphare S (Bio-Rad);
GigaCap S 650M (TOSOH);
GigaCap CM 650M (TOSOH);
TOYOPERAL SP 650 M (TOSOH);
TOYOPERAL CM 650 M (TOSOH);
TOYOPERAL SP 650 S (TOSOH);
TOYOPERAL CM 650 S (TOSOH);
SP sepharose FF (GE Healthcare);
SP sepharose HP (GE Healthcare);
Capto S (GE Healthcare);
ProRes S (Merk-Millipore);
Capt S Impres (GE Healthcare);
SOURCE 30S (GE Healthcare);
Eshumuno CPX (Merk-Millipore);
Nuvia S (Bio-Rad); and
Nuvia HRS (Bio-Rad).

Examples of columns for hydrophobic interaction chromatography include, but are not limited to,
Phenyl Sepharose High Performance (GE Healthcare);
Butyl Sepharose High Performance (GE Healthcare);
Phenyl Sepharose 6 Fast Flow (GE Healthcare);
Butyl-S Sepharose 6 Fast Flow (GE Healthcare);
Butyl Sepharose 4 Fast Flow (GE Healthcare);
Octyl Sepharose 4 Fast Flow (GE Healthcare);
Capto Phenyl ImpRes (GE Healthcare);
Capto Phenyl (GE Healthcare);
Capto Butyl (GE Healthcare);
Capto Octyl (GE Healthcare);
Fractogel Phenyl (Merck Millipore Corp.);
Fractogel Propyl (Merck Millipore Corp.);
TOYOPEARL Butyl (TOSOH Corp.);
TOYOPEARL Ether (TOSOH Corp.);
TOYOPEARL Hexyl (TOSOH Corp.);
TOYOPEARL Phenyl (TOSOH Corp.);
TOYOPEARL PPG (TOSOH Corp.);
TOYOPEARL SuperButyl (TOSOH Corp.);
TOYOPEARL Butyl-600 (TOSOH Corp.); and
Macro-Prep HIC (Bio-Rad Laboratories Inc.).

Examples of columns for multimodal chromatography include, but are not limited to,
CHT TypeI 40 um (Bio-Rad);
CHT TypeI 80 um (Bio-Rad);
CHT TypeII 40 um (Bio-Rad);
CHT TypeII 80 um (Bio-Rad);
CFT TypeI 40 um (Bio-Rad);
CFT TypeII 40 um (Bio-Rad);
Capto MMC (GE Healthcare);
Capto Adhere (GE Healthcare);
"TryptopHan Immobilized Resin" (TOSOH); and
MEP HyperCel (PALL).

Furthermore, in the purification steps, a step for virus inactivation and filtration can be carried out after the purification step using a precipitation technique of the present invention and before carrying out the purification step by polishing column chromatography.

In addition to the methods for purifying compositions comprising antibodies, the present invention also provides methods for producing compositions comprising purified antibodies or compositions comprising antibodies from which impurities have been removed, which can be obtained by the purification method of the present invention; methods for producing pharmaceutical compositions using these compositions; and compositions and pharmaceutical compositions comprising antibodies that can be obtained by these production methods.

Features of the methods for producing compositions comprising purified antibodies or compositions comprising antibodies from which impurities have been removed according to the present invention include, for example, substituting the purification step that uses an anionic polymer for conventional protein A column chromatography and/or protein G column chromatography to achieve a high impurity removal rate without the use of such column chromatographic methods. In this case, the impurity content ratio of a composition that has undergone all of the purification steps can be represented as a mass ratio with respect to the antibody, and this mass ratio is preferably 0.2 or less, more preferably 0.1 or less, and even more preferably 0.05 or less. A specific example of a composition comprising antibodies of the present invention is, but not limited to, a composition which comprises an antibody whose pI is 5.0 to 7.0, has a mass ratio of impurity content to the antibody that is 0.2 or less, and does not contain protein A and/or protein G as impurities.

The mass ratios can be measured, for example, by an HCP analysis method, a DNA analysis method, and also by using the monomer, HMW, and LMW (the impurities are HMW and LMW which are not the monomer) in size extrusion chromatography (SEC).

The purified antibodies or pharmaceutical compositions comprising compositions comprising the antibodies of the present invention may be solution formulations (antibody-containing solution formulations) or lyophilized agents. Solution formulations of the present invention include solutions before lyophilization in the production process of lyophilized formulations, or solutions that have been redissolved. The solution formulations of the present invention are preferably solution formulations produced without including a lyophilizing step in the production process (solution formulations that are not redissolved solutions of a lyophilized formulation). Lyophilized agents of the present invention can be obtained by lyophilizing the solution formulations of the present invention by methods known to those skilled in the art.

As pharmaceutically acceptable carriers and/or additives, formulations of the present invention can contain additives such as cryoprotective agents, suspending agents, solubilizing agents, isotonizing agents, preservatives, adsorption-preventing agents, diluents, excipients, pH adjusters, analgesics, sulfur-containing reducing agents, and antioxidants, and carriers.

Examples of cryoprotective agents include, but are not limited to, sugars such as trehalose, sucrose, and sorbitol.

Examples of solubilizing agents include, but are not limited to, polyoxyethylene hydrogenated castor oil, Polysorbate 80, nicotinic acid amide, polyoxyethylene sorbitan monolaurate, macrogol, and castor oil fatty acid ethyl ester.

Examples of isotonizing agents include, but are not limited to, sodium chloride, potassium chloride, and calcium chloride.

Examples of preservatives include, but are not limited to, methyl p-hydroxybenzoate, ethyl p-hydroxybenzoate, sorbic acid, phenol, cresol, and chlorocresol.

Examples of adsorption-preventing agents include, but are not limited to, human serum albumin, lecithin, dextran, ethyleneoxide-propyleneoxide copolymer, hydroxypropyl cellulose, methylcellulose, polyoxyethylene hydrogenated castor oil, and polyethylene glycol.

Examples of sulfur-containing reducing agents include, but are not limited to, N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and compounds with sulfhydryl groups such as thioalkanoic acids that have one to seven carbon atoms.

Examples of antioxidants include, but are not limited to, erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium hydrogen sulfite, sodium sulfite, triamyl gallate, and propyl gallate, or chelating agents such as disodium ethylenediamine tetraacetate (EDTA), sodium pyrophosphate, and sodium metaphosphate.

A pharmaceutical composition or formulation of the present invention can be administered either orally or parenterally, but generally, it is administered via a parenteral route. Specifically, it is administered by injection, transdermal, transmucosal, transnasal, transpulmonary administration, or such. Examples of the types of injections include subcutaneous injection, intravenous injection, intramuscular injection, and such which enable systemic or local administration. In the case of subcutaneous injection, there is a limit to the amount of injection solution, but the amount of antibody administered per injection can be a large amount (100 mg to 200 mg or so). Therefore, formulations of the present invention are particularly suitable for use in subcutaneous administration (injection).

All prior art documents cited in the specification are incorporated herein by reference.

EXAMPLES

Herein below, the present invention will be specifically described with reference to the Examples, but the scope of the invention is not limited to these Examples.

The following antibodies were used in the Examples.

Mab1: an anti-NR10 (IL-31 receptor) antibody, which is a fully humanized NS22 antibody produced by the method described in Example 12 of WO 2009/072604. The antibody class is IgG2, and the antibody was produced by lowering the pI value to 5.6 through amino acid sequence modifications. The amino acid sequences of the Mab1 antibody are represented by SEQ ID NO: 3 (H chain) and SEQ ID NO: 4 (L chain).

Mab2: an anti-IL-6 receptor antibody described in WO 2009/041621, whose pI value has been changed to 5.8 by modifying the amino acids of tolicizumab (SEQ ID NO: 5 (H chain) and SEQ ID NO: 6 (L chain)). The amino acid sequences of the Mab2 antibody are represented by SEQ ID NO: 1 (H chain) and SEQ ID NO: 2 (L chain).

Mab3 (ACE910): the bispecific antibody Q499-z1213327-z119/L404-k described in WO2012/067176. It binds specifically to both F.IX/F.IXa and F.X, and has a function that substitutes for the function of F.IXa to promote F.X activation (F.Xa production-promoting function) and its pI value is 6.9. The common name is Emicizumab, and it is registered as the International Nonproprietary Name (INN) (see, chem.sis.nlm.nih.gov/chemidplus/m/1610943-06-0).

Example 1-1: Removal of Impurities from a Mab1-Containing Composition (HCCF) by an Anionic Polymer (at pH 4.0 and 4.2)

Experiments in which the method of purification by an anionic polymer is applied to an antibody-producing cell culture fluid (HCCF) that uses CHO cells, were carried out in Example 1-1 (the same applies to Examples 1-2 to 1-4 below).

An acetic acid solution was added to 10 mL of Mab1 HCCF to adjust pH to 4.0 and 4.2. HCCF was obtained by expressing the antibody by a method known to those skilled in the art using a CHO cell stable expression line and removing cells from the antibody-producing cell culture fluid by known methods.

PVS described below was added as an anionic polymer to produce a ratio of antibody mass $g_{antibody}$ to PVS mass $g_{polymer}$ ($g_{polymer}/g_{antibody}$) of 0.1, and this mixture was stirred for 15 minutes or more using a stir bar.

Name: Poly(vinylsulfonic acid, sodium salt) solution
Concentration: 25 wt % (=316.8 mg/mL)
Model number: 278424-250ML
Lot: 02220LDV
Manufacturer: Sigma-Aldrich The obtained solution containing impurities precipitated by PVS was centrifuged at 3000 rpm for ten minutes using a centrifuge. The supernatant was collected, and this was filtered through a PES filter having a pore size of 0.22 μm. The HCP and DNA concentrations of the obtained filtrate were measured. The results of measuring the HCP and DNA concentrations, and the yields obtained from this operation are shown in Table 1. The yield was calculated from the ratio of the input concentration and the output concentration since the volume of the solution hardly changes (yield=output concentration/input concentration×100; unless otherwise stated below, the yield was calculated using this method).

TABLE 1

PVS impurity precipitation results from Mab1 HCCF

|  | HCP (ng/mg) | DNA (pg/mg) | Yield (%) |
|---|---|---|---|
| HCCF | 1.5E+06 | 8.8E+05 | — |
| PVS pool (pH 4.0) | 2.3E+04 | <3.4E+00 | 79.3 |
| PVS pool (pH 4.2) | 3.9E+04 | <2.8E+00 | 95.6 |

The row for "HCCF" in Table 1 shows the content ratios of HCP and DNA in terms of ng/mg and pg/mg, respectively, before performing the removal by precipitation using PVS. (1.5E+06 is an alternative expression for 1.5×10⁶ ng/mg.) Furthermore, the rows for "PVS pool (pH 4.0)" and "PVS pool (pH 4.2)" show the content ratios of HCP and DNA under the conditions of pH 4.0 and 4.2, respectively, after performing the removal by precipitation using PVS. The yield shows the yield of the antibody in percentage (%) after the removal by precipitation using PVS as compared to before the removal (the same applies hereafter).

Table 1 shows that Log reduction values for HCP and DNA removal from Mab1 HCCF were, respectively, 1.6 to 1.8 and 4 or more, using the impurity removal method by precipitation with an anionic polymer under conditions at pH 4.0 or 4.2. The yields were 79.3% at pH 4.0 and 95.6% at pH 4.2, and this showed that a high antibody yield is secured even after removal of impurities by an anionic polymer.

Example 1-2: Removal of Impurities from a Mab1-Containing Composition (HCCF) by an Anionic Polymer (at Each pH)

To confirm the pH dependency of the effects elucidated in Example 1-1, an acetic acid solution was added to 10 mL of Mab1 HCCF to adjust pH to 3.0, 3.5, 3.8, 4.0, 4.2, 4.4, 4.5, and 5.0, respectively. PVS (Catalog No.: 278424-250ML) was added to produce a ratio of antibody mass $g_{antibody}$ to PVS mass $g_{polymer}$ ($g_{polymer}/g_{antibody}$) of 0.1, and this mixture was stirred for 15 minutes or more using a stir bar. The obtained solution containing impurities precipitated by PVS was centrifuged at 3000 rpm for ten minutes using a centrifuge. The supernatant was collected, and this was filtered through a Polyethersulfone (PES) filter having a pore size of 0.22 μm. The HCP and DNA concentrations in the obtained filtrate were measured. The results of measuring the HCP and DNA concentrations when the ratio between the antibody mass $g_{antibody}$ and PVS mass $g_{polymer}$ is 0.1, and the yields obtained from this operation are shown in Table 2 and FIG. 1.

TABLE 2

|  | HCP (ng/mg) | DNA (pg/mg) | Antibody concentration (mg/mL) | Yield (%) |
|---|---|---|---|---|
| Input | 1.5E+06 | 8.8E+05 | 1.84 | — |
| PVS pH 3.8 | 2.8E+04 | <1.8E+01 | 0.55 | 29.9 |
| PVS pH 4.0 | 2.2E+04 | <6.3E+00 | 1.59 | 86.4 |
| PVS pH 4.0 | 2.7E+04 | 4.2E+00 | 1.26 | 68.4 |
| PVS pH 4.2 | 8.7E+04 | 7.0E+00 | 1.82 | 98.9 |
| PVS pH 4.4 | 3.1E+05 | <5.3E+00 | 1.92 | 104.3 |

High removal rates of HCP and DNA were confirmed at pH 3.8 to pH 4.4 according to Table 2. Furthermore, according to FIG. 1, at pH values of 3.5 or higher, or in particular, at 3.8 or higher, part of the antibodies were found to remain without being precipitated even after addition of the anionic polymer.

Example 1-3: Removal of Impurities from a Mab1-Containing Composition (HCCF) by an Anionic Polymer (at Each pH, and PVS Mass Ratio of 0.01)

Figure 2:
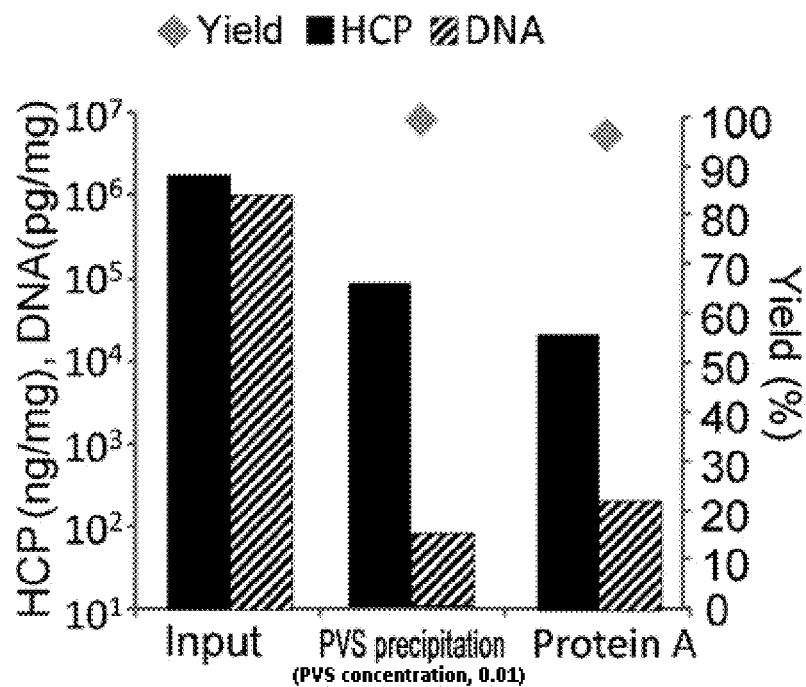
FIG. 2 shows a graph indicating the results of removing HCP and DNA by the respective purification processes (PVS: 0.01).

To examine the influence of the added amount of the anionic polymer on the effects elucidated in Examples 1-1 and 1-2, an acetic acid solution was added to 10 mL of Mab1 HCCF to adjust pH to 3.8, 4.0, 4.2, and 4.4. PVS (Catalog No.: 278424-250ML) was added to produce a ratio of antibody mass $g_{antibody}$ to PVS mass $g_{polymer}$ ($g_{polymer}/g_{antibody}$) of 0.01, and this mixture was stirred for 15 minutes or more using a stir bar. The obtained fraction containing impurities precipitated by PVS was centrifuged at 3000 rpm for ten minutes using a centrifuge. The supernatant was collected, and this was filtered through a PES filter having a pore size of 0.22 μm. The HCP and DNA concentrations in the obtained filtrate were measured. The results of measuring the HCP and DNA concentrations when the ratio between the antibody mass $g_{antibody}$ and the PVS mass $g_{polymer}$ is 0.01, and the yields obtained from this operation are shown in Table 3. Furthermore, FIG. 2 shows the HCP/DNA content ratio of the input and the antibody yields, comparing the values obtained after the removal by precipitation using PVS of this Example to the values after purification by protein A column chromatography.

TABLE 3

|  | HCP (ng/mg) | DNA (pg/mg) | Concentration (mg/mL) | Yield (%) |
|---|---|---|---|---|
| CM Input | 1.5E+06 | 8.8E+05 | 1.84 | — |
| PVS pH 3.8 | 9.5E+04 | 4.1E+03 | 1.53 | 83.3 |
| PVS pH 4.0 | 8.7E+04 | 8.8E+01 | 1.81 | 98.6 |

TABLE 3-continued

| | HCP (ng/mg) | DNA (pg/mg) | Concentration (mg/mL) | Yield (%) |
|---|---|---|---|---|
| PVS pH 4.2 | 2.1E+05 | 3.6E+01 | 1.88 | 102.2 |
| PVS pH 4.4 | 5.3E+05 | 7.4E+01 | 1.90 | 103.3 |

From Table 3, high removal rates of HCP and DNA were confirmed at pH 3.8 to pH 4.2 when the amount of added PVS was set to 0.01. Furthermore, it was revealed that high yields can be maintained in a wide range of pH values.

According to FIG. 2, high HCP and DNA removal rates and antibody yields are achieved by the removal by precipitation using an anionic polymer, which are equivalent to or more than those from the purification step using protein A column chromatography.

Example 1-4: Removal of Impurities from a Mab1-Containing Composition (HCCF) by an Anionic Polymer (at Each PVS Mass Ratio)

Figure 3:
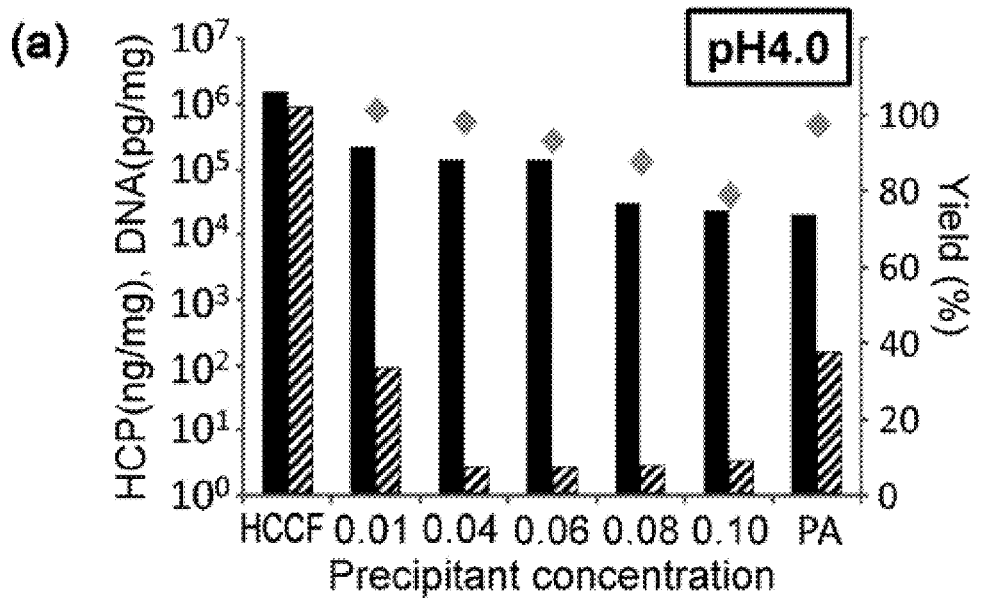
FIGS. 3A and 3B show graphs indicating the examination results in the optimization of PVS concentration for precipitation of impurities using PVS at pH 4.0 (FIG. 3(A)) and pH 4.2 (FIG. 3(B)).
Figure 3:
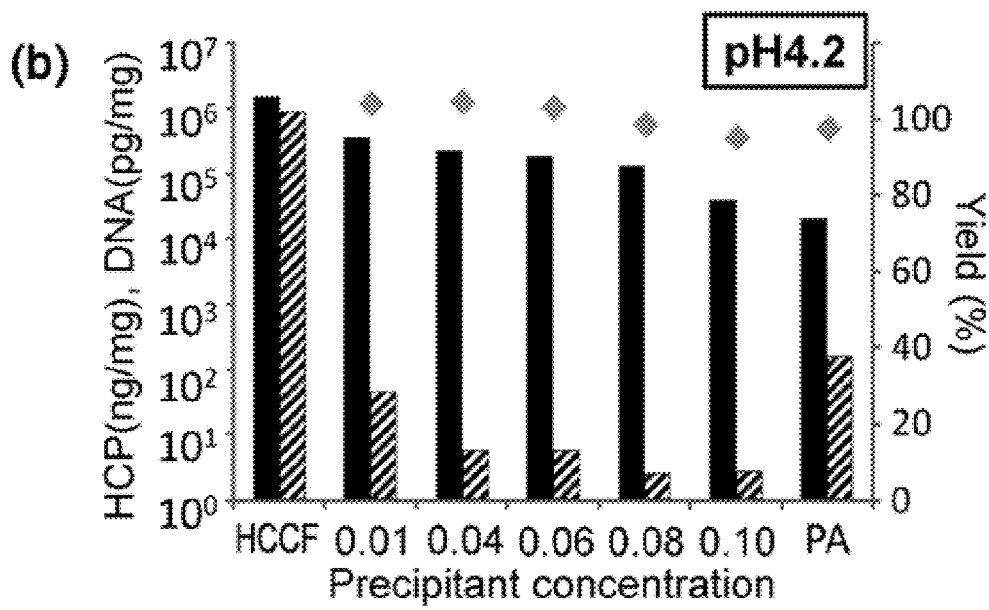

For detailed examination of the influence of the amount of added PVS in Example 1-3, an acetic acid solution was added to 10 mL of Mab1 HCCF to adjust pH to 4.0 or 4.2. PVS (Catalog No.: 278424-250ML) was added to produce ratios of antibody mass $g_{antibody}$ to PVS mass $g_{polymer}$ ($g_{polymer}/g_{antibody}$) of 0.01, 0.04, 0.06, 0.08, and 0.10, respectively, and the mixture was stirred for 15 minutes or more using a stir bar. The obtained solution containing impurities precipitated by PVS was centrifuged at 3000 rpm for ten minutes using a centrifuge. The supernatant was collected, and this was filtered through a Polyethersulfone (PES) filter having a pore size of 0.22 μm. The HCP and DNA concentrations in the obtained filtrate were measured. Table 4 and FIG. 3(A) show the results of measuring PVS, HCP, and DNA concentrations when pH was 4.0 and the yields obtained from this operation, comparing with those from the method of purification by protein A column chromatography. Furthermore, Table 5 and FIG. 3(B) show the results of measuring PVS, HCP, and DNA concentrations when pH was 4.2 and the yields obtained from this operation, comparing with those obtained from the method of purification by protein A column chromatography. "PA" in FIGS. 3(A) and 3(B) shows the yield from the step of removing impurities by protein A column chromatography, and the remaining amounts of HCP and DNA in the fractions from this step.

TABLE 4

| PVS concentration | HCP (4.0) | DNA (4.0) | Yield |
|---|---|---|---|
| 0 | 1.5E+06 | 8.8E+05 | |
| 0.01 | 2.3E+05 | No Data | 101.6 |
| 0.04 | 1.4E+05 | No Data | 98.4 |
| 0.06 | 1.4E+05 | 2.9E+00 | 93.5 |
| 0.08 | 3.1E+04 | <3.1E+00 | 88.0 |
| 0.10 | 2.3E+04 | <3.4E+00 | 79.3 |
| Protein A | 2.0E+04 | 1.6E+02 | 97.8 |

TABLE 5

| PVS concentration | HCP (4.2) | DNA (4.2) | Yield |
|---|---|---|---|
| 0 | 1.5E+06 | 8.8E+05 | |
| 0.01 | 3.5E+05 | 4.5E+01 | 104.5 |
| 0.04 | 2.3E+05 | 6.0E+00 | 104.9 |
| 0.06 | 1.8E+05 | 6.0E+00 | 103.3 |

TABLE 5-continued

| PVS concentration | HCP (4.2) | DNA (4.2) | Yield |
|---|---|---|---|
| 0.08 | 1.3E+05 | <2.7E+00 | 98.9 |
| 0.10 | 3.9E+04 | <2.8E+00 | 95.6 |
| Protein A | 2.0E+04 | 1.6E+02 | 97.8 |

Tables 4 and 5 and FIGS. 3(A)-3(B) show that when the mass ratio of PVS to Mab1 is in the range of 0.08 to 0.1 and pH is 4.0, or when the mass ratio of PVS to Mab1 is 0.1 and pH is in the range of 4.0 to 4.2, the abilities to remove HCP and DNA that are equivalent to or more than those of the purification method using protein A column chromatography can be achieved.

In Examples 1-1 to 1-4, the relationship between pH and the mass ratio was examined using PVS as the anionic polymer; however, these results are not limited to PVS, and similar effects can be expected when a polymer having similar functions, for example PSS or PAA, is used as the anionic polymer.

Example 2-1: Removal of Impurities from a Mab1-Containing Composition (Protein A Elution Fraction) by an Anionic Polymer In Example 2-1, experiments are carried out applying the method of purification using an anionic polymer to an elution fraction obtained after performing the step of purifying by protein A column chromatography on an antibody-producing cell culture fluid (HCCF) that uses CHO cells.

A 2M Tris solution was added to 10 mL of the Protein A elution fraction of Mab1 to adjust pH to 4.5. PVS was added to produce a ratio of antibody mass $g_{antibody}$ to PVS mass $g_{polymer}$ ($g_{polymer}/g_{antibody}$) of 0.008 or 0.006, and this mixture was stirred for 15 minutes or more using a stir bar. The obtained solution containing impurities precipitated by PVS was centrifuged at 3000 rpm for ten minutes using a centrifuge. The supernatant was collected, and this was filtered through a PES filter having a pore size of 0.22 μm. The HCP and DNA concentrations in the obtained filtrate (PVS pool) were measured. The results of measuring the HCP and DNA concentrations, and the yields obtained from this operation are shown in Table 6. In addition, the amount of monomer in the PVS pool was calculated by the area percentage method using size exclusion chromatography (SEC).

TABLE 6

PVS impurity precipitation results from Mab1 Protein A elution fraction

| | Yield (%) | HCP (ng/mg) | DNA (pg/mg) | Monomer (%) |
|---|---|---|---|---|
| Protein A elution fraction | — | 7.8E+03 | 1.2E+03 | 97.9 |
| PVS pool ($g_{polymer}/g_{antibody}$: 0.008) | 72.6 | 9.5E+00 | <6.7E-01 | 99.4 |
| PVS pool ($g_{polymer}/g_{antibody}$: 0.006) | 90.9 | 4.7E+01 | <5.1E-01 | 99.3 |

According to Table 6, it was found that Log reduction values for HCP and DNA removal from Protein A elution fraction were, respectively, 2.2 to 2.9 and 3 or more, using the impurity removal method by precipitation with PVS. It was also revealed that the amount of monomer can be increased.

Example 2-2: Removal of Impurities from a Mab1-Containing Composition (Protein A Elution Fraction) by an Anionic Polymer (Results of Precipitation of Impurities in the PVS/Low pH/Neutralized Fraction and AEX Elution Fraction)

In Example 2-2, experiments are carried out applying the method of purification using an anionic polymer to an elution fraction obtained after performing the step of purifying by protein A column chromatography on an antibody-producing cell culture fluid (HCCF) that uses CHO cells, and performing further purification by virus inactivation/filtration and anion exchange (AEX) column chromatography.

A 2M Tris solution was added to approximately 100 mL of the Protein A elution fraction of Mab1 to adjust pH to 4.5. PVS was added to produce a ratio of antibody mass $g_{antibody}$ to PVS mass $g_{polymer}$ ($g_{polymer}/g_{antibody}$) of 0.01, and this mixture was stirred for 15 minutes or more using a stir bar. The obtained solution containing impurities precipitated by PVS was filtered through a glass fiber filter and a PES filter having a pore size of 0.22 μm. Imitating the virus inactivation step in the actual production and purification process, 1 mol/L hydrochloric acid was added to the obtained filtrate, and pH was maintained at 3.6 for one hour or more. The maintained antibody solution was neutralized to pH 7.0 using 2 mol/L Tris, and this was left to stand for 6 hours or more. Subsequently, this was filtered through a PES filter having a pore size of 0.22 μm to obtain a PVS/low pH/neutralized fraction. The HCP, DNA, and Protein A concentrations of the PVS/low pH/neutralized fraction was measured. The yield of the PVS/low pH/neutralization step was calculated from the equation: (input concentration×input volume)/(output concentration×output volume)×100. The obtained PVS/low pH/neutralized fraction was purified by a method known to those skilled in the art, including anion exchange (AEX) chromatography, and an AEX elution fraction was obtained. The HCP, DNA, and Protein A concentrations of the AEX elution fraction were measured.

TABLE 7

| | Yield (%) | HCP (ng/mg) | DNA (pg/mg) | Protein A (ng/mg) |
|---|---|---|---|---|
| Protein A elution fraction | — | 2.7E+04 | 4.6E+02 | 4.3 |
| PVS/Low pH/ neutralized fraction | 69.8 | 3.4E+01 | <5.8E−01 | 2.1 |
| AEX elution fraction | 82.0 | <15 (<8)** | <9.1E−01 | <0.4 |

**The values in the parentheses are measurement values of concentrated solutions of the AEX elution fraction According to Table 7, it was found that, with a series of operations of PVS, low pH, and neutralization, Log reduction values for HCP and DNA removal were, respectively, 2.9 and 2.9. Furthermore, it was also revealed that all of the HCP, DNA, and Protein A impurities can be decreased below the quantitation limit.

Examples 2-1 and 2-2 used PVS as the anionic polymer, and its combined use with column chromatography techniques such as Protein A column chromatography was examined. These results are not limited to the case with PVS, and a polymer having a similar anionic polymer function, such as PSS and PAA, can be expected to yield similar effects.

Example 3-1: Removal of Impurities from a Mab2-Containing Composition (HCCF) by an Anionic Polymer In the experiments of Example 3-1, the method of purification by an anionic polymer was applied to an antibody-producing cell culture fluid (HCCF) that uses CHO cells (the same applies to Example 3-2 below).

An acetic acid solution was added to 10 mL of Mab2 HCCF to adjust pH to 4.6. PVS was added to produce a ratio of antibody mass $g_{antibody}$ to PVS mass $g_{polymer}$ ($g_{polymer}/g_{antibody}$) of 0.04, and this mixture was stirred for 15 minutes or more using a stir bar. The obtained solution containing the impurities precipitated by PVS was centrifuged at 3000 rpm for ten minutes using a centrifuge. The supernatant was collected, and this was filtered through a PES filter having a pore size of 0.22 μm. The HCP and DNA concentrations in the obtained filtrate were measured. The results of measuring the HCP and DNA concentrations and the yields obtained from this operation are shown in Table 8.

TABLE 8

| | Yield (%) | HCP (ng/mg) | DNA (pg/mg) |
|---|---|---|---|
| Input (HCCF) | — | 1.3E+06 | 8.0E+05 |
| PVS pool | 86.2 | 1.1E+05 | 8.1E+00 |

According to Table 8, it was found that Log reduction values for HCP and DNA removal from Mab2 HCCF were, respectively, 1.1 and 5.0, using the impurity removal method by precipitation with an anionic polymer, and a high yield was accomplished.

Accordingly, high removal rates of HCP and DNA and high antibody collection rate were also confirmed for Mab2 at pH 4.0, i.e., pI of Mab2 minus 1.8.

Example 3-2: Removal of Impurities from a Mab2-Containing Composition (HCCF) by an Anionic Polymer (at Each pH)

Figure 4:
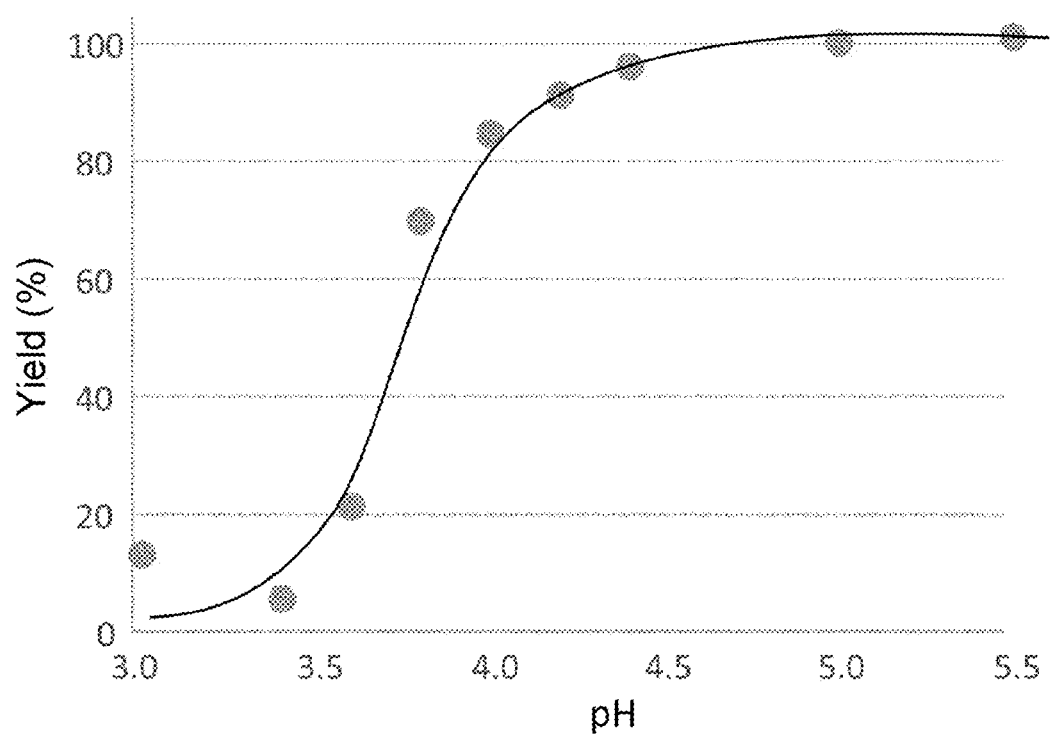
FIG. 4 shows a graph indicating the antibody yield at each pH value.

To confirm the pH dependency of the effects elucidated in Example 3-1, an acetic acid solution was added to 10 mL of Mab2 HCCF to adjust pH to 3.0, 3.4, 3.6, 3.8, 4.0, 4.2, 4.4, 5.0, and 5.5, respectively. PVS was added to produce a ratio of antibody mass $g_{antibody}$ to PVS mass $g_{polymer}$ ($g_{polymer}/g_{antibody}$) of 0.04, and this mixture was stirred for 15 minutes or more using a stir bar. The obtained solution containing impurities precipitated by PVS was centrifuged at 3000 rpm for ten minutes using a centrifuge. The supernatant was collected, and this was filtered through a PES filter having a pore size of 0.22 μm. The HCP and DNA concentrations in the obtained filtrate were measured. The results of measuring the HCP and DNA concentrations and the yields obtained from this operation at the respective pH values are shown in Table 9 and FIG. 4.

TABLE 9

| | HCP (ng/mg) | DNA (pg/mg) | Antibody concentration (mg/mL) | Yield (%) |
|---|---|---|---|---|
| Input | 1.3E+06 | 8.0E+05 | 1.89 | — |
| PVS pH 3.0 | 3.4E+05 | 9.0E+04 | 0.277 | 14.7 |
| PVS pH 3.4 | 1.3E+06 | 7.4E+05 | 0.132 | 7.0 |
| PVS pH 3.6 | 2.2E+05 | 1.1E+05 | 0.431 | 22.8 |

TABLE 9-continued

|  | HCP (ng/mg) | DNA (pg/mg) | Antibody concentration (mg/mL) | Yield (%) |
| --- | --- | --- | --- | --- |
| PVS pH 3.8 | 8.4E+04 | 1.5E+02 | 1.35 | 71.4 |
| PVS pH 4.0 | 1.1E+05 | 8.1E+00 | 1.63 | 86.2 |
| PVS pH 4.2 | 2.0E+05 | 9.0E+00 | 1.75 | 92.6 |
| PVS pH 4.4 | 2.2E+05 | 1.6E+01 | 1.84 | 97.4 |
| PVS pH 5.0 | 4.2E+05 | 3.5E+02 | 1.92 | 101.6 |
| PVS pH 5.5 | 5.6E+05 | 5.3E+02 | 1.94 | 102.6 |

High removal rates of HCP and DNA were confirmed at pH 3.0 to 5.0, preferably at pH 3.6 to 4.6, and more preferably at pH 3.8 to 4.4, according to Table 9. Furthermore, according to FIG. 4, at pH values of 3.5 or higher, or particularly at 3.8 or higher, part of the antibodies were found to remain without being precipitated even after addition of the anionic polymer.

Example 4-1: Removal of Impurities from a Mab2-Containing Composition (Protein A Elution Fraction) by an Anionic Polymer In Example 4-1, experiments are carried out applying the method of purification using an anionic polymer to an elution fraction obtained after performing the step of purifying by protein A column chromatography on an antibody-producing cell culture fluid (HCCF) that uses CHO cells.

A 2M Tris solution was added to 10 mL of the Protein A elution fraction of Mab2 to adjust pH to 4.7. PVS was added to produce a ratio of antibody mass $g_{antibody}$ to PVS mass $g_{polymer}$ ($g_{polymer}/g_{antibody}$) of 0.008, and this mixture was stirred for 15 minutes or more using a stir bar. The obtained solution containing impurities precipitated by PVS, was centrifuged at 3000 rpm for ten minutes using a centrifuge. The supernatant was collected, and this was filtered through a Polyethersulfone (PES) filter having a pore size of 0.22 µm. The HCP and DNA concentrations in the obtained filtrate were measured. The results of measuring the HCP and DNA concentrations, and the yield obtained from this operation are shown in Table 10.

TABLE 10

|  | Yield (%) | HCP (ng/mg) | DNA (pg/mg) |
| --- | --- | --- | --- |
| Pretein A elution fraction | — | 3.7E+03 | 1.0E+02 |
| PVS pool | 89.2 | 4.3E+02 | <1.5E+00 |

According to Table 10, it was found that, with the precipitation of impurities using PVS, Log reduction rates for removal of HCP and DNA from the Protein A elution fraction of Mab2 were, respectively, 0.9 and 1.8.

Example 4-2: Removal of Impurities from a Mab2-Containing Composition (Protein A Elution Fraction) by an Anionic Polymer (at Each pH)

A 2M Tris solution was added to 10 mL of the Protein A elution fraction of Mab2 to adjust pH to 4.1, 4.3, 4.5, and 4.7. PVS was added to produce a ratio of antibody mass $g_{antibody}$ to PVS mass $g_{polymer}$ ($g_{polymer}/g_{antibody}$) of 0.08, and this mixture was stirred for 15 minutes or more using a stir bar. The obtained solution containing impurities precipitated by PVS was centrifuged at 3000 rpm for ten minutes using a centrifuge. The supernatant was collected, and this was filtered through a Polyethersulfone (PES) filter having a pore size of 0.22 µm. The HCP and DNA concentrations in the obtained filtrate were measured. The results of measuring the HCP and DNA concentrations at the respective pH values, and the yields obtained from this operation are shown in Table 11.

TABLE 11

|  | Concentration (mg/mL) | Yield (%) | HCP (ng/mg) | DNA (pg/mg) |
| --- | --- | --- | --- | --- |
| Input | 18.5 | — | 3.7E+03 | 1.0E+02 |
| PVS pH 4.1 | 18.0 | 97.2 | 3.6E+03 | 1.1E+02 |
| PVS pH 4.3 | 18.4 | 99.5 | 2.6E+03 | 9.5E+01 |
| PVS pH 4.5 | 18.4 | 99.5 | 1.4E+03 | 7.8E+00 |
| PVS pH 4.7 | 16.5 | 89.2 | 4.3E+02 | <1.5E+00 |

Removal of HCP and DNA were confirmed at pH 4.5 to 4.7, according to Table 11.

Example 5: Removal of Impurities from a Mab3-Containing Composition (Protein A Elution Fraction) by an Anionic Polymer (at Each pH)

Acetic acid was added to 10 mL of a low pH/neutralization pool of Mab3 (pI: 6.9) to adjust pH to 4.0. PVS was added to produce a ratio of antibody mass $g_{antibody}$ to PVS mass $g_{polymer}$ ($g_{polymer}/g_{antibody}$) of 0.015, and this mixture was stirred for 15 minutes or more using a stir bar. The obtained solution containing impurities precipitated by PVS was centrifuged at 3000 rpm for ten minutes using a centrifuge. The supernatant was collected, and this was filtered through a Polyethersulfone (PES) filter having a pore size of 0.22 µm. The HCP and DNA concentrations in the obtained filtrate were measured. The results of measuring the HCP and DNA concentrations at the respective pH values and the yield obtained from this operation are shown in Table 12.

TABLE 12

|  | Conc. (mg/mL) | Yield (%) | HCP (ng/mg) | DNA (pg/mg) |
| --- | --- | --- | --- | --- |
| Low pH/ neutralization pool | 19.1 | — | 5.0E+03 | 1.3E+02 |
| PVS pool | 13.4 | 70.1 | 7.3E+01 | <3.7E−01 |

Table 12 shows that Log reduction values for HCP and DNA removal from Mab3 HCCF were, respectively, 1.8 and 2.5 or more, using the impurity removal method by precipitation with an anionic polymer under conditions at pH 4.0. The yield was 70.1% at pH 4.0 and this showed that a certain level of antibody yield is secured even after removal of impurities by an anionic polymer.

DISCUSSION

According to the results of Examples 1 to 5, it would be desirable to add the anionic polymer at pH lower than the pI of the antibody, or more preferably at pH of the pI of the antibody minus 1. When pH is too high, insolubilization of impurities by the anionic polymer becomes insufficient, and the HCP/DNA removal rates will be lowered. Meanwhile, it would be desirable to add the anionic polymer at a pH value of 3.5 or higher, or more preferably 3.8 or higher. When pH is lower than this value, the antibodies will be easily precipitated by the anionic polymer, and the antibody yield will tend to be decreased.

Furthermore, considering the results of the Examples, the anionic polymer may be added within the range of pH 3.5 to 5.0, or more preferably pH 3.8 to 5.0. To adjust pH to a value optimum for adding the anionic polymer, a low antibody pI is desirable. Generally, it is desirable for a low-pI antibody to have pI of 3.0 to 8.0, and more practically, pI of 5.0 to 7.0.

Furthermore, when HCCF is subjected to purification using an anionic polymer (PVS), the amount of added PVS is within the range of 0.01 to 0.1 at a mass ratio to the antibody.

Applications:

An application of the present invention is, for example, substituting the purification using an anionic polymer for a conventional column chromatography technique, or using the purification using an anionic polymer together with a conventional column chromatography technique.

Figure 5:
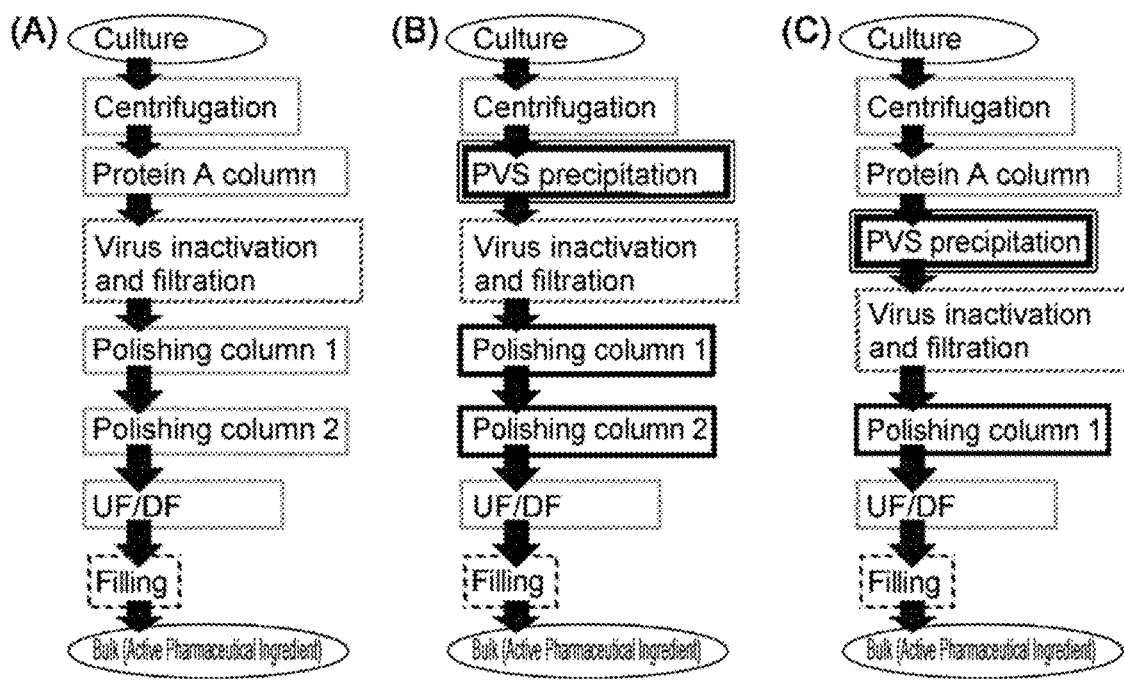
FIGS. 5A-5C show flow charts indicating the antibody purification processes that utilize the present invention.

As indicated in FIG. 5(A), a conventional antibody purification is carried out by performing the following steps in order:

(1) obtaining HCCF by subjecting a CHO cell culture liquid to centrifugation, and then to filtration using a filter such as a Depth filter or a sterilizing filter;

(2) obtaining a Protein A elution fraction by purifying HCCF by Protein A column chromatography;

(3) obtaining a low pH/neutralized fraction by subjecting the Protein A elution fraction to virus inactivation at low pH, neutralization, and then filtration using a Depth filter, a sterilizing filter and such (virus inactivation and filtration);

(4) obtaining a polishing column chromatography step (1) fraction, by purifying the low pH/neutralized fraction by polishing column chromatography;

(5) obtaining a polishing column chromatography step (2) fraction, by purifying the fraction from polishing column chromatography step (1) by subsequent polishing column chromatography;

(6) obtaining an antibody solution having a prescribed concentration and prescribed buffer components by concentrating the polishing column chromatography step (2) fraction using ultrafiltration/diafiltration, and then exchanging buffers; and (7) obtaining a bulk (API: Active Pharmaceutical Ingredient) by filtering this antibody solution through a sterilizing filter, and then aliquoting the solution.

On the other hand, as shown in FIG. 5(B), the technique of precipitation by using an anionic polymer (for example, PVS) of the present invention can be used as a substitute for Protein A column chromatography. In this case, an antibody can be purified, for example, by the following flow of steps:

(1') obtaining HCCF by subjecting a CHO cell culture liquid to centrifugation, and then to filtration using a filter such as a Depth filter and a sterilizing filter;

(2') obtaining an anionic polymer impurity precipitation fraction by adding an anionic polymer (for example, PVS) to HCCF to precipitate impurities, and then filtering this through a Depth filter, or such;

(3') obtaining a low pH/neutralized fraction by subjecting the fraction to virus inactivation at low pH, neutralization, and then filtration using a sterilizing filter;

(4') obtaining a polishing column chromatography step (1) fraction, by purifying the low pH/neutralized fraction by polishing column chromatography;

(5' obtaining a polishing column chromatography step (2) fraction, by purifying the polishing column chromatography step (1) fraction by subsequent polishing column chromatography; and (6') performing steps (6) and (7) mentioned above in order by a method similar to that described in FIG. 5(A). To remove the anionic polymer, at least one of polishing column chromatography steps (1) and (2) is desirably a step that uses anion exchange column chromatography.

Alternatively, as shown in FIG. 5(C), the technique of precipitation by using an anionic polymer (for example, PVS) of the present invention can be used as a substitute for polishing column chromatography. In this case, an antibody can be purified, for example, by the following flow of steps.

For example, a Protein A elution fraction is obtained by performing steps (1) and (2) mentioned above by a method similar to that described in FIG. 5(A);

(3") obtaining an anionic polymer impurity precipitation fraction by adding an anionic polymer (for example, PVS) to this elution fraction to precipitate impurities, and then filtering this through a Depth filter or such;

(4") obtaining a low pH/neutralized fraction by subjecting the fraction to virus inactivation at low pH, neutralization, and then filtration using a sterilizing filter;

(5") obtaining a polishing column chromatography step (1) fraction, by purifying the low pH/neutralized fraction by polishing column chromatography;

(6") obtaining an antibody solution having a prescribed concentration and prescribed buffer components by concentrating the polishing column chromatography step (1) fraction by ultrafiltration/diafiltration, and then exchanging buffers; and (7") performing the step (7) mentioned above by a method similar to that described in FIG. 5(A). To remove the anionic polymer, the first polishing column chromatography step is desirably a step that uses anion exchange column chromatography.

INDUSTRIAL APPLICABILITY

The present invention provides methods for purification that can efficiently remove antibody aggregates and impurities contained in a composition comprising antibodies. Purification methods of the present invention are useful in the production of biopharmaceuticals for which a high purity is required.

The invention claimed is:

1. A method for purifying a composition comprising an antibody, which comprises the steps of:
   (a) preparing a composition comprising an antibody in such a state that the composition comprises an anionic polymer at pH lower than the pI of the antibody; and
   (b) removing an impurity insolubilized by the anionic polymer from the composition.

2. The method of claim 1, wherein step (a) is preparing the composition in such a state that the composition comprises an anionic polymer at pH lower than or equal to the pI of the antibody minus one.

3. The method of claim 1, wherein step (a) is preparing the composition in such a state that the composition comprises an anionic polymer at pH of 3.5 to less than the pI of the antibody.

4. The method of claim 1, wherein step (a) is preparing the composition in such a state that the composition comprises an anionic polymer at pH of 3.5 to the pI of the antibody minus one or lower.

5. A method for purifying a composition comprising an antibody, which comprises the steps of:
   (a) preparing a composition comprising an antibody in such a state that the composition comprises an anionic polymer at pH of 3.5 to 5.0; and
   (b) removing an impurity insolubilized by the anionic polymer from the composition.

6. The method of claim 5, wherein step (a) is preparing the composition in such a state that the composition comprises an anionic polymer at pH of 3.8 to 5.0.

7. The method of claim 1, wherein the pI of the antibody is 3.0 to 8.0.

8. The method of claim 1, wherein the pI of the antibody is 5.0 to 7.0.

9. The method of claim 1, wherein the anionic polymer is polyvinylsulfonic acid (PVS), polyacrylic acid (PAA), or polystyrenesulfonic acid (PSS).

10. The method of claim 1, wherein step (b) is removing an impurity insolubilized by an anionic polymer using a filter.

11. The method of claim 1, wherein the antibody has been produced in a CHO cell.

12. The method of claim 1, wherein the antibody is a monoclonal antibody and is a humanized antibody or a human antibody.

13. The method of claim 12, wherein the antibody is an anti-tissue factor antibody, anti-IL-6 receptor antibody, anti-IL-6 antibody, anti-HM1.24 antigen monoclonal antibody, anti-parathyroid hormone-related peptide antibody (anti-PTHrP antibody), anti-glypican-3 antibody, anti-ganglioside GM3 antibody, anti-TPO receptor agonist antibody, antibody functionally substituting for coagulation factor VIII, anti-IL31 receptor antibody, anti-HLA antibody, anti-AXL antibody, anti-CXCR4 antibody, anti-NR10 antibody, or bispecific antibody against factor IX or factor IXA and factor X.

14. The method of claim 1, wherein the impurity is a host cell-derived protein (HCP) or a DNA.

15. A method for removing an impurity from an antibody-producing cell culture fluid (HCCF) using the method of claim 1.

16. The method of claim 15, wherein the anionic polymer is polyvinylsulfonic acid (PVS) and step (a) is preparing the composition in such a state that the composition comprises polyvinylsulfonic acid (PVS) at a mass ratio of 0.01 to 0.1 to the antibody.

17. The method of claim 15, which further comprises a purification step that uses any one or a combination of anion exchange column chromatography, cation exchange column chromatography, hydrophobic interaction column chromatography, and multimode chromatography.

18. A method for removing an impurity from a protein A elution fraction or protein G elution fraction using the method of claim 1, wherein the protein A elution fraction or protein G elution fraction is a product purified from an antibody-producing cell culture fluid (HCCF) by protein A column chromatography or protein G column chromatography.

19. A method for producing a composition comprising an antibody in which the mass ratio of an impurity to the antibody has been lowered to 0.2 or less, wherein the method comprises removing the impurity by the method of claim 1, and does not comprise a purification step using protein A column chromatography or protein G column chromatography.

20. A method for producing a pharmaceutical composition, which comprises producing a composition comprising an antibody by the method of claim 19, and formulating said composition by admixing the composition with a pharmaceutically acceptable carrier or additive.

* * * * *